US008088596B2

(12) United States Patent
Zeng et al.

(10) Patent No.: US 8,088,596 B2
(45) Date of Patent: Jan. 3, 2012

(54) METHOD OF MICROORGANISM DETECTION USING CARBOHYDRATE AND LECTIN RECOGNITION

(75) Inventors: Xiangqun Zeng, Rochester, MI (US); Zhihong Shen, Auburn Hills, MI (US)

(73) Assignee: Oakland University, Rochester, MI (US)

( * ) Notice: Subject to any disclaimer, the term of this patent is extended or adjusted under 35 U.S.C. 154(b) by 1046 days.

(21) Appl. No.: 11/973,772

(22) Filed: Oct. 9, 2007

(65) Prior Publication Data

US 2008/0193965 A1    Aug. 14, 2008

Related U.S. Application Data

(60) Provisional application No. 60/850,561, filed on Oct. 10, 2006.

(51) Int. Cl.
*C12Q 1/04* (2006.01)
*C12N 11/00* (2006.01)
*C12M 1/34* (2006.01)

(52) U.S. Cl. ........ 435/34; 435/174; 435/287.1; 435/810

(58) Field of Classification Search .................. None
See application file for complete search history.

(56) References Cited

U.S. PATENT DOCUMENTS

| | | | |
|---|---|---|---|
| 4,236,893 A | 12/1980 | Rice | |
| 4,242,096 A | 12/1980 | Oliveira et al. | |
| 4,246,344 A | 1/1981 | Silver, III | |
| 4,314,821 A | 2/1982 | Rice | |
| 4,659,658 A * | 4/1987 | McCarthy et al. | 435/7.36 |
| 4,735,906 A | 4/1988 | Bastiaans | |
| 4,788,466 A | 11/1988 | Paul et al. | |
| 4,999,284 A | 3/1991 | Ward et al. | |
| 5,117,192 A | 5/1992 | Hurd | |
| 5,201,215 A | 4/1993 | Granstaff et al. | |
| 5,233,261 A | 8/1993 | Wajid | |
| 5,282,925 A | 2/1994 | Jeng et al. | |
| 5,314,830 A | 5/1994 | Anderson et al. | |
| 5,484,626 A | 1/1996 | Storjohann et al. | |
| 5,616,827 A | 4/1997 | Simmermon et al. | |
| 5,706,840 A | 1/1998 | Schneider | |
| 5,795,993 A | 8/1998 | Pfeifer et al. | |
| 5,885,402 A | 3/1999 | Esquibel | |
| 5,932,953 A | 8/1999 | Drees et al. | |
| 6,087,187 A | 7/2000 | Wiegland et al. | |
| 6,106,149 A | 8/2000 | Smith | |
| 6,190,035 B1 | 2/2001 | Smith | |
| 6,439,765 B2 | 8/2002 | Smith | |
| 6,492,601 B1 | 12/2002 | Cain et al. | |
| 6,647,764 B1 | 11/2003 | Paul et al. | |
| 6,706,977 B2 | 3/2004 | Cain et al. | |
| 6,848,299 B2 | 2/2005 | Paul et al. | |
| 6,890,486 B2 | 5/2005 | Penelle | |
| 7,005,294 B2 * | 2/2006 | Lehmann | 435/287.8 |
| 7,341,841 B2 * | 3/2008 | Metzger et al. | 435/7.2 |
| 2006/0014232 A1 | 1/2006 | Inagawa et al. | |
| 2010/0248283 A1 | 9/2010 | Xiao et al. | |

OTHER PUBLICATIONS

Plomer, M.; Guilbault, G. G.; Hock, B. "Development of a piezoelectric immunosensor for the detection of enterobacteria." Enzyme and Microbial Technoroly 1992, 14, 230-235.

Ivnitski, D.; Abdel-Hamid, I.; Atanasov, P.; Wilkins, E. "Biosensors for detection of pathogenic bacteria." Biosensors and Bioelectronics 1999, 14, 599-624.

Pathirana, S. T.; Barbaree, J.; Chin, B. A.; Bartell, M. G.; Neely, W. C.; Vodyanoy, V. "Rapid and sensitive biosensor for *Salmonella*." Biosensors and Bioelectronics 2000, 15, 135-141.

Fung, Y. S.; Wong, Y. Y. "Self-Assembled Monolayers as the Coating in a Quartz Piezoelectric Crystal Immunosensor To Detect *Salmonella* in Aqueous Solution." Analytical Chemistry 2001, 73, 5302-5309.

Kim, N.; Park, I.-S. "Application of a flow-type antibody sensor to the detection of *Escherichia coli* in various foods." Biosensors and Bioelectronics 2003, 18, 1101-1107.

Su, X.-L.; Li, Y. "A self-assembled monolayer-based piezoelectric immunosensor for rapid detection of *Escherichia coli* O157:H7." Biosensors and Bioelectronics 2004, 19, 563-574.

Wong, Y. Y.; Ng, S. P.; Ng, M. H.; Si, S. H.; Yao, S. Z.; Fung, Y. S. "Immunosensor for the differentiation and detection of *Salmonella* species based on a quartz crystal microbalance." Biosensors and Bioelectronics 2002, 17, 676-684.

Minunni, M.; Mascini, M.; Carter, R. M.; Jacobs, M. B.; Lubrano, G. J.; Guilbault, G. G. "A quartz crystal microbalance displacement assay for *Listeria monocytogenes*." Analytica Chimica Acta 1996, 325, 169-174.

Bao, L. L.; Deng, L.; Nie, L. H.; Yao, S. Z.; Wei, W. Z. "Determination of microorganisms with a quartz crystal microbalance sensor." Analytica Chimica Acta 1996, 319, 97-101.

Otto, K.; Elwing, H.; Hermansson, M. "Effect of ionic strength on initial interactions of *Escherichia coli* with surfaces, studied on-line by a novel quartz crystal microbalance technique." Journal of Bacteriology 1999, 181, 5210-5218.

Zhou, T.; Marx, K. A.; Warren, M.; Schulze, H.; Braunhut, S. J. "The Quartz Crystal Microbalance as a Continuous Monitoring Tool for the Study of Endothelial Cell Surface Attachment and Growth." Biotechnology Progress 2000, 16, 268-277.

Mrksich, M. "A surface chemistry approach to studying cell adhesion." Chemical Society Reviews 2000, 29, 267-273.

Smith, E. A.; Thomas, W. D.; Kiessling, L. L.; Corn, R. M. Journal of the American Chemical Society 2003, 125, 6140.

Culf, A. S.; Cuperlovic-Culf, M.; Ouellette, R. J. "Carbohydrate Microarrays: Survey of Fabrication Techniques." OMICS: A Journal of Integrative Biology 2006, 10, 289-310.

Manimala, J. C.; Roach, T. A.; Li, Z.; Gildersleeve, J. C. "High-throughput carbohydrate microarray profiling of 27 antibodies demonstrates widespread specificity problems." Glycobiology %R 10.1093/glycob/cwm047 2007, 17, 17C-23.

(Continued)

*Primary Examiner* — David Naff
(74) *Attorney, Agent, or Firm* — Ian C. McLeod

(57) ABSTRACT

Methods of binding and detecting a microorganism on a solid substrate. The microorganism is bound on a solid substrate covalently bound to a capture agent having a saccharide moiety. A lectin capable of binding to the microorganism and the saccharide moiety of the capture agent is added to the sample to bind the microorganism on the solid substrate. Further provided are biosensor devices, such as a quartz crystal microbalance (QCM) device or a surface plasmon resonance (SPR) device, that incorporate the solid substrate for the detection of microorganisms.

6 Claims, 24 Drawing Sheets

OTHER PUBLICATIONS

Kanoelani T. Pilobello, L. K. D. S. L. K. M. "Development of a Lectin Microarray for the Rapid Analysis of Protein Glycopatterns." ChemBioChem 2005, 6, 985-989.

Nangia-Makker, P.; Conklin, J.; Hogan, V.; Raz, A. "Carbohydrate-binding proteins in cancer, and their ligands as therapeutic agents." Trends in Molecular Medicine 2002, 8, 187-192.

Stevenson, G.; Neal, B.; Liu, D.; Hobbs, M.; Packer, N. H.; Batley, M.; Redmond, J. W.; Lindquist, L.; Reeves, P. "Structure of the O-Antigen of *Escherichia-coli*-K-12 and the Sequence of Its Rfb Gene-Cluster." Journal of Bacteriology 1994, 176, 4144-4156.

Lee, Y. C.; Lee, R. T. "Carbohydrate-Protein Interactions: Basis of Glycobiology." Accounts of Chemical Research 1995, 28, 321-7.

Brewer, C. F.; Miceli, M. C.; Baum Linda, G. "Clusters, bundles, arrays and lattices: novel mechanisms for lectin-saccharide-mediated cellular interactions." Current opinion in structural biology 2002, 12, 616-23.

Williams, S. J.; Davies, G. J. "Protein—carbohydrate interactions: learning lessons from nature." Trends in biotechnology 2001, 19, 356-62.

Lindhorst, T. K. "Artificial multivalent sugar ligands to understand and manipulate carbohydrate-protein interactions." Topics in Current Chemistry 2002, 218, 201-235.

Houseman, B. T.; Mrksich, M. "Model systems for studying polyvalent carbohydrate binding interactions." Topics in Current Chemistry 2002, 218, 1-44.

Liang, R.; Loebach, J.; Horan, N.; Ge, M.; Thompson, C.; Yan, L.; Kahne, D. "Polyvalent binding to carbohydrates immobilized on an insoluble resin." Proceedings of the National Academy of Sciences of the United States of America 1997, 94, 10554-10559.

Mathai Mammen, S.-K. C. G. M. W. "Polyvalent Interactions in Biological Systems: Implications for Design and Use of Multivalent Ligands and Inhibitors." Angewandte Chemie International Edition 1998, 37, 2754-2794.

Shinohara, Y.; Hasegawa, Y.; Kaku, H.; Shibuya, N. "Elucidation of the mechanism enhancing the avidity of lectin with oligosaccharides on the solid phase surface." Glycobiology 1997, 7, 1201-1208.

Kolb, H. C.; Finn, M. G.; Sharpless, K. B. "Click chemistry: Diverse chemical function from a few good reactions." Angewandte Chemie-International Edition 2001, 40, 2004-+.

Ratner, D. M.; Adams, E. W.; Disney, M. D.; Seeberger, P. H. "Tools for glycomics: Mapping interactions of carbohydrates in biological systems." Chembiochem 2004, 5, 1375-1383.

Mann, D. A.; Kanai, M.; Maly, D. J.; Kiessling, L. L. "Probing Low Affinity and Multivalent Interactions with Surface Plasmon Resonance: Ligands for Concanavalin A." Journal of the American Chemical Society 1998, 120, 10575-10582.

Ostuni, E.; Chapman, R. G.; Liang, M. N.; Meluleni, G.; Pier, G.; Ingber, D. E.; Whitesides, G. M. "Self-assembled monolayers that resist the adsorption of proteins and the adhesion of bacterial and mammalian cells." Langmuir 2001, 17, 6336-6343.

Fung, Y. S.; Wong, Y. Y. "Self-assembled monolayers as the coating in a quartz piezoelectric crystal immunosensor to detect *Salmonella* in aqueous solution." Analytical Chemistry 2001, 73, 5302-5309.

Jelinek, R.; Kolusheva, S. "Carbohydrate Biosensors." Chem.Rev. 2004,104,5987-6015. (33) Poxton, I. R. "Antibodies to lipopolysaccharide." Journal of Immunological Methods 1995, 186, 1-15.

Poxton, I. R. "Antibodies to lipopolysaccharide." Journal of Immunological Methods 1995, 186, 1-15.

Feizi, T.; Fazio, F.; Chai, W.; Wong Chi, H. "Carbohydrate microarrays—a new set of technologies at the frontiers of glycomics." Current opinion in structural biology 2003, 13, 637-45.

Pohl, Nicola L. "Array Methodology Singles Out Pathogenic Bacteria." Nature Chemical Biology vol. 2, No. 3, 2006, 125-126.

Deisingh, A.K.; Thompson, M. "Detection of Infectious and Toxigenic Bacteria." Analyst, 2002, 127, 567-581.

Disney, M.D.; Seeberger, P.H. "The Use of Carbohydrate Microarrays to Study Carbohydrate-Cell Interactions and to Detect Pathogens." Chemistry & Biology, V. 11, 1701-1707, 2004.

Angeloni, S.; Ridet, J.L.; Kusy, N.; Gao, H.; Crevoisier, F.; Guinchard, S.; Kochhar, S.; Sigrist, H.; and Sprenger, N. "Glycoprofiling with Micro-Arrays of Glycoconjugates and Lectins." Glycobiology, V. 15, No. 1, 31-41, 2005.

Zheng, T.; Peelen, D., and Smith, L.M. "Lectin Arrays for Profiling Cell Surface Carbohydrate Expression." J. Am. Chem. Soc. (2005), 127, p. 9982-9983.

Horlacher, T. and Seeberger, P.H. "The Utility of Carbohydrate Microarrays in Glycomics." OMICS A Journal of Integrative Biology, V. 10, No. 4 (2006), p. 490-498.

Hsu, K.-L.; Pilobello, K.T. and Mahal, L.K. "Analyzing the Dynamic Bacterial Glycome with a Lectin Microarray Approach." Nature Chemical Biology, V. 2, No. 3 (2006), p. 153-157.

Disney, M.D.; Seeberger, P.H. "Catching Bacteria with Sugar." Chemistry & Biology, V. 11, (2004), p. 1602-1604.

Benz, I. and Schmidt, A. "Never Say Never Again: Protein Glycosylation in Pathogenic Bacteria." Molecular Microbiology (2002) 45(2), 267-276.

Fukui, S.; Feizi, T.; Galustian, C.; Lawson, A.M. and Chai, W. "Oligosaccharide Microarrays for High-Throughput Detection and Specificity Assignments of Carbohydrate-Protein Interactions."Nature Biotechnology, V. 20, 2002,p. 1011-1017.

Pilobello, K.T.; Krishnamoorthy, L.; Slawek, D. and Mahal, L.K. "Development of a Lectin Microarray for the Rapid Analysis of Protein Glycopatterns." ChemoBioChem 2005, 6, 985-989.

Houseman, B.T. and Mrksich, M. "Carbohydrate Arrays for the Evaluation of Protein Binding and Enzymatic Modification." Chemistry & Biology, V. 9, 443-454, Apr. 2002.

Chen, S.; Zheng, T.; Shortreed, M.R.; Alexander, C. and Smith, L.M. "Analysis of Cell Surface Carbohydrate Expression Patterns in Normal and Tumorigenic Human Breast Cell Lines Using Lectin Arrays." Analytical Chemistry, V. 79, N. 15, (2007), p. 5698-5702.

Wang, D.; Liu, S.; Trummer, B.J.; Deng, C. and Wang, A. "Carbohydrate Microarrays for the Recognition of Cross-Reactive Molecular Markers of Microbes and Host Cells." Nature Biotechnology, V. 20, (2002), p. 275-281.

* cited by examiner

METHOD OF MICROORGANISM DETECTION USING CARBOHYDRATE AND LECTIN RECOGNITION

CROSS-REFERENCE TO RELATED APPLICATIONS

This application claims benefit to U.S. Provisional Application Ser. No. 60/850,561, filed Oct. 10, 2006, which is incorporated herein by reference in its entirety.

STATEMENT REGARDING FEDERALLY SPONSORED RESEARCH OR DEVELOPMENT

This research was supported by grants from the National Institute of Health (NIH) (4R33 EB000672-02). The U.S. Government has certain rights to this invention.

BACKGROUND OF THE INVENTION (1) Field of the Invention

The present invention relates generally to microorganism binding with a substrate bound capture agent having a saccharide moiety and a lectin. In particular, the present invention relates to a method of binding a microorganism on the substrate using the capture agent and lectin in an assay method and test kit.

(2) Description of the Related Art

Rapid methods for bacterial detection are essential in food, industrial, environmental monitoring, clinical diagnostics and biodefense to allow faster decisions to be made with respect to food poisoning, water contamination, the presence of disease and, therefore, treatment options. Most conventional methods (e.g. plating and culturing, biochemical tests, microscopy, flow cytometry, luminescence) are time consuming, often requiring 1-2 days to obtain results. Although much faster detection methods such as immunosensors or DNA chips are becoming available, they have failed to gain wide acceptance due to the high user expertise required, high cost of labeling reagents, and low stability of antibody and DNA recognition elements. As a result, a rapid, quantitative, sensitive and specific method for one step bacterial detection is highly sought after.

Cell surface carbohydrates (glycans) and adhesin molecules are major components of the outer surface of cells and are often characteristic of the cell types. Many adhesin molecules are lectins that have carbohydrate binding activities. Glycans and adhesins are the first interface to the biotic and abiotic environment of the cell. The interactions of glycans with carbohydrate binding proteins (lectins) are perhaps the most significant and fundamental molecular recognition events in biological systems including bacterial pathogenesis, tumor cell metastasis, and inflammation. To understand the biological roles of a particular carbohydrate or to evaluate a lectin adhesin as a disease biomarker, one must to determine when, where and how much a carbohydrate and/or lectin adhesin is expressed. The expression of carbohydrate structures changes dramatically during cell development and the carbohydrates from different organisms display tremendous variations in structure and function. A similar situation exists for bacterial cell surface lectin adhesin expression. As a result, the carbohydrate and/or lectin adhesin expression levels are extremely difficult to measure and present a formidable challenge for studying and characterizing their roles in cell biology.

In recent years, advances in the fields of combinatorial carbohydrate synthesis and automated carbohydrate synthesis have made available a great number of glycans for study. ([32]Jelinek, R.; Kolusheva, S. "Carbohydrate Biosensors." Chem. Rev. 2004, 104, 5987-6015) Carbohydrate microarrays were developed to study the carbohydrate-cell interaction and to detect pathogens.[(14)-(16)] Carbohydrate-arrays allow for the analysis of protein carbohydrate interactions in a variety of glycobiology systems, but they do not allow the direct examination of changes in glycosylation. Therefore, the bound lectin arrays that allow quick assess of bacterial cell surface carbohydrate compositions were developed. Unfortunately similar to many protein arrays, they suffer some loss of binding activity in the coupling of lectin to the arrays. The large sizes of lectins also increase their susceptibility to proteases and encourage non-specific binding. Most previously reported carbohydrate and lectin arrays are one dimensional and use fluorescence label for detection. Fluorescence labeling of the bacteria cells requires additional steps. The presence of the labels themselves can introduce additional interferences to the "true" binding process. Fluorescent detection can also suffer from high background fluorescence which may produce false positive results. U.S. Patent Application Publication No. 2006/0014232 to Inagawa et al. teaches immobilization of biomolecules, provided with at least one tag, to a substrate. The substrate has binding sites for the tags and activated reactive groups capable of forming covalent bonds with the biomolecules. The biomolecules can be immobilized to prepare a sensor chip used for surface plasmon resonance or quartz-crystal microbalance techniques. The prior art does not teach the use of lectins to bind a microorganism to the substrate.

While the related art teach bacterial detection methods, there still exists a need for rapid, quantitative, sensitive and specific microorganisms analysis and detection method and test kit. See references: (([17]Nangia-Makker, P.; Conklin, J. Hogan, V.; Raz, A. "Carbohydrate-binding proteins in cancer, and their ligands as therapeutic agents." Trends in Molecular Medicine 2002, 8, 187-192.) ([18]Stevenson, G.; Neal, B.; Liu, D.; Hobbs, M.; Packer, N. H.; Batley, M.; Redmond, J. W.; Lindquist, L.; Reeves, P. "Structure of the O-Antigen of *Escherichia-Coli*-K-12 and the Sequence of Its Rfb Gene-Cluster." Journal of Bacteriology 1994, 176, 4144-4156); ([19]Lee, Y. C.; Lee, R. T. "Carbohydrate-Protein Interactions: Basis of Glycobiology." Accounts of Chemical Research 1995, 28, 321-7); ([21]Williams and Davies, Trends in biotechnology 2001, 19, 356-62); ([22]Lindhorst, T. K. "Artificial multivalent sugar ligands to understand and manipulate carbohydrate-protein interactions." Topics in Current Chemistry 2002, 218, 201-235); ([23]Houseman, B. T.; Mrksich, M. "Model systems for studying polyvalent carbohydrate binding interactions." Topics in Current Chemistry 2002, 218, 1-44); ([24]Liang, R.; Loebach, J.; Horan, N.; Ge, M.; Thompson, C.; Yan, L.; Kahne, D. "Polyvalent binding to carbohydrates immobilized on an insoluble resin." Proceedings of the National Academy of Sciences of the United States of America 1997, 94, 10554-10559); ([25]Mathai Mammen, S.-K. C. G. M. W. "Polyvalent Interactions in Biological Systems: Implications for Design and Use of Multivalent Ligands and Inhibitors." Angewandte Chemie International Edition 1998, 37, 2754-2794); ([26]Shinohara, Y.; Hasegawa, Y.; Kaku, H.; Shibuya, N. "Elucidation of the mechanism enhancing the avidity of lectin with oligosaccharides on the solid phase surface." Glycobiology 1997, 7, 1201-1208); ([27]Kolb, H. C.; Finn, M. G.; Sharpless, K. B. "Click Chemistry: Diverse chemical function from a few good reactions." Angewandte Chemie-International Edition 2001, 40, 2004-+); ([28]Ratner, D. M.; Adams, E. W.; Disney, M. D.; Seeberger, P. H. "Tools for glycomics: Mapping interactions of carbohydrates in biological systems." *Chembiochem* 2004, 5, 1375-1383); ([29]Mann, D. A.; Kanai, M.; Maly, D. J.; Kiessling, L. L. "Probing Low Affinity and Multivalent Interactions with Surface Plasmon Resonance: Ligands for Concanavalin A." *Journal of the American Chemical Society* 1998, 120, 10575-10582); ([30]Ostuni, E.; Chapman, R. G.; Liang, M. N.; Meluleni, G.; Pier, G.; Ingber, D. E.; Whitesides, G. M. "Self-assembled monolayers that resist the adsorption of proteins and the adhesion of bacterial and mammalian cells." *Langmuir* 2001, 17, 6336-6343); ([31]Fung, Y. S.; Wong, Y. Y. "Self-assembled monolayers as the coating in a quartz piezoelectric crystal immunosensor to detect *Salmonella* in aqueous solution." *Analytical Chemistry* 2001, 73, 5302-5309); ([33]Poxton, I. R. "Antibodies to lipopolysaccharide." *Journal of Immunological Methods* 1995, 186, 1-15) and ([34]Feizi, T.; Fazio, F.; Chai, W.; Wong Chi, H. "Carbohydrate microarrays—a new set of technologies at the frontiers of glycomics." *Current opinion in structural biology* 2003, 13, 637-45).

OBJECTS

It is therefore an object of the present invention to provide a reliable method and test kit for analysis and detection of a microorganism. It is further an object of the present invention to provide an economical assay to profile bacterial surface carbohydrate and lectin expression. These and other objects will become increasingly apparent by reference to the following description and the drawings.

SUMMARY OF THE INVENTION

The present invention provides a method of attaching a microorganism to a solid substrate comprising: providing the substrate having a surface covalently bound to a capture agent having a saccharide moiety, the microorganism in a sample, and an unbound lectin capable of binding to the microorganism and to the saccharide moiety of the capture agent; and applying the sample and a lectin to the substrate with the capture agent having the saccharide moiety, for a time to bind the lectin to the saccharide moiety of the capture agent, and the lectin to the microorganism to attach the microorganism to the solid substrate. In further embodiments, the saccharide moiety is a mannose based saccharide. In further still embodiments, the lectin is concanavalin A (ConA) and the microorganism is an *E. coli* species. In still further embodiments, the lectin is present in an amount that binds to multiple of lipopolysaccharides exposed on a cell wall of the microorganism and to the saccharide moieties. In further still embodiments, the lectin is present in an amount that binds to multiple of lipopolysaccharides exposed on a cell wall of the microorganism and to the saccharide moieties and wherein the saccharide moieties also bind to other parts of the microorganism.

The present invention further provides a method of detecting a microorganism in a sample comprising: providing (1) a biosensor device for detecting the microorganism in the sample comprising a solid substrate having a surface covalently bound to a capture agent having a saccharide moiety, (2) the sample, and (3) an unbound lectin capable of binding to the microorganism and to the saccharide moiety of the capture agent; applying the sample and an unbound lectin to the solid substrate with the capture agent having the saccharide moiety, for a time to bind the lectin to the saccharide moiety of the capture agent and the lectin to the microorganism to attach the microorganism to the solid substrate; and detecting the microorganism attached to the solid substrate with the biosensor device. In further embodiments, the substrate is provided as a component in a quartz crystal microbalance (QCM) device, a surface plasmon resonance (SPR) device or an impedance device. In still further embodiments, a polyethylene glycol thiol is applied as a blocking agent to the solid substrate prior to applying the sample to reduce nonspecific adsorption to the solid substrate. In further still embodiments, the lectin is present in an amount which binds to multiple of lipopolysaccharides on an exposed cell wall of the microorganism.

The present invention further provides a kit for detection of a microorganism in a sample comprising: a solid substrate with a capture agent having a saccharide moiety covalently bound to a surface of the solid substrate; and an unbound lectin capable of binding the microorganism and the capture agent, wherein when the microorganism in the sample and the lectin capable of binding to the microorganism and to the saccharide moiety of the capture agent are applied to the solid substrate, the lectin binds the microorganism and the saccharide moiety of the capture agent so as to bind the microorganism to the solid substrate for the detection. In further embodiments, the surface of the solid substrate is metallic. In further still embodiments, the substrate is provided as a component in a quartz crystal microbalance (QCM) device, a surface plasmon resonance (SPR) device or an impedance device. In still further embodiments, the lectin is present in an amount which binds to multiple of lipopolysaccharides on an exposed cell wall of the microorganism and to the saccharide moieties. In still further embodiments, the kit includes a blocking agent to prevent non-specific binding. In further still embodiments, the substrate is a component of a multiple array of different lectins or polysaccharides bound to the substrate. In still further embodiments, the substrate is a component of a multiple array of different lectins or polysaccharides bound to the substrate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
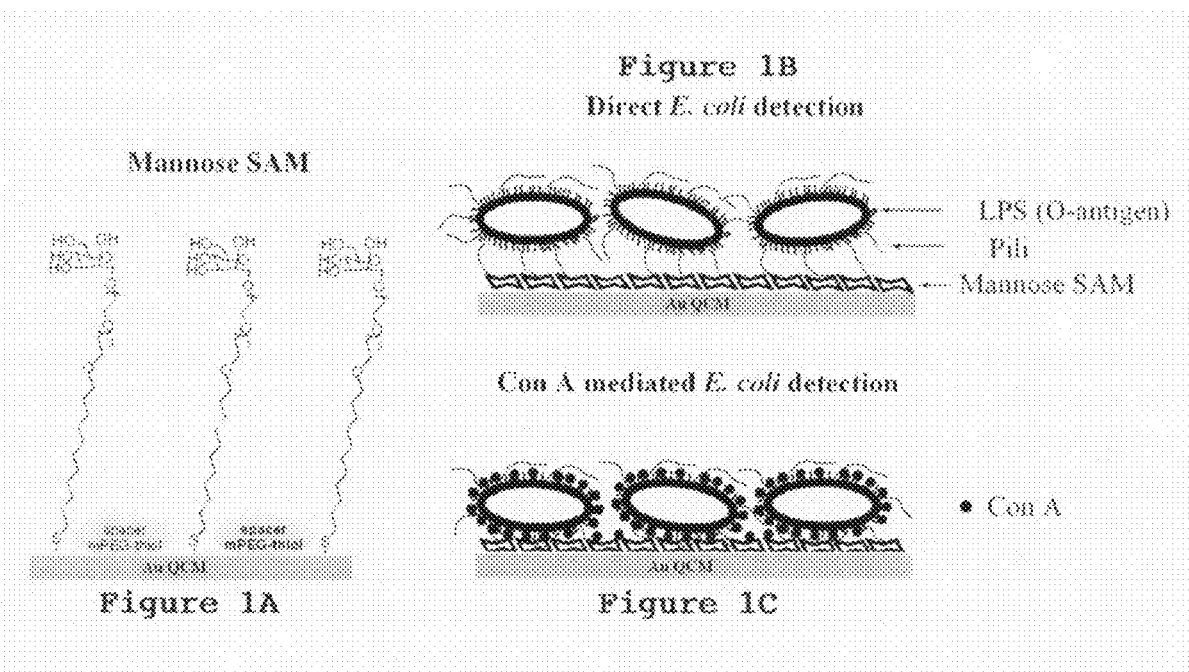
FIGS. 1A, 1B and 1C are schematic representations of mannose SAMs and *E. coli* detection: 1A) Mannose SAM; 1B) Direct *E. coli* detection; 1C) Con A mediated *E. coli* detection.

All patents, patent applications, government publications, government regulations, and literature references cited in this specification are hereby incorporated herein by reference in their entirety. In case of conflict, the present description, including definitions, will control.

High percentages of harmful microbes or their secreting toxins bind to specific carbohydrate sequences on human cells at the recognition and attachment sites. A number of studies also show that lectins react with specific structures of bacteria and fungi. We take advantage of the fact that a high percentage of micro-organisms have both carbohydrate and lectin binding pockets at their surface. It is demonstrated here for the first time that a carbohydrate non-label mass sensor in combination with lectin-bacteria recognition can be used for detection of high molecular weight bacterial targets with remarkably high sensitivity and enhanced specificity. A functional mannose self assembled monolayer in combination with lectin Con A was used as molecular recognition elements for the detection of *E. coli* W1485 using Quartz Crystal Microbalance (QCM) as a transducer. The multivalent binding of Con A to the *E. coli* surface receptor (lipopolysaccharide (LPS)) favors the strong adhesion of *E. coli* to mannose modified QCM surface by forming bridges between these two. As a result, the contact area between cell and QCM surface increases and leads to rigid and strong attachment that enhances the binding between *E. coli* and the mannose receptor. The results show a significant improvement of the sensitivity and specificity of carbohydrate QCM biosensor with a detection limit of a few hundred bacterial cells and a linear range from $7.5 \times 10^2$ to $7.5 \times 10^7$ cells/mL that is four decades wider than the mannose alone QCM sensor. The change of damping resistances for *E. coli* adhesion experiments was no more than 1.4%, suggesting that the bacterial attachment was rigid, rather than a viscoelastic behavior. Little non-specific binding was observed for *Staphylococcus aureus* and other proteins (Fetal Bovine serum, *Erythrina cristagalli* lectin). This approach not only overcomes the challenges of applying QCM technology for bacterial detection but also increases the binding of bacteria to their carbohydrate receptor through bacterial surface binding lectins that significantly enhanced specificity and sensitivity of QCM biosensors. Combining carbohydrate and lectin recognition events with an appropriate QCM transducer yields sensor devices highly suitable for the fast, reversible and straightforward on-line screening and detection of bacteria in food, water, clinical and biodefense areas.

The term "saccharide" as used herein refers to a carbohydrate, including monosaccharides, disaccharides, and polysaccharides.

The term "microorganism" as used herein refers to any microorganism, including but not limited to, bacteria and fungi.

The term "bacteria" as used herein refers to include both gram-positive and gram-negative bacteria.

The term "gram-negative bacteria" as used herein refer to any gram-negative bacteria such as, but not limited to, proteobacteria, including *Escherichia coli, Salmonella, Vibrio, Helicobacter* and other Enterobacteriaceae, *Pseudomonas, Moraxella, Helicobacter, Stenotrophomonas, Bdellovibrio,* acetic acid bacteria, *Legionella* and others. Gram-negative bacteria also include cyanobacteria, spirochaetes, green sulfur and green non-sulfur bacteria. Gram-negative cocci include, but are not limited to, organisms that cause sexually transmitted disease (*Neisseria gonorrhoeae*), meningitis (*Neisseria meningitidis*), and respiratory symptoms (*Moraxella catarrhalis*). Gram-negative bacilli include, but are not limited to, baccilli causing respiratory problems (*Hemophilus influenzae, Klebsiella pneumoniae, Legionella pneumophila, Pseudomonas aeruginosa*), urinary problems (*Escherichia coli, Proteus mirabilis, Enterobacter cloacae, Serratia marcescens*), and gastrointestinal problems (*Helicobacter pylori, Salmonella enteritidis, Salmonella typhi*).

The term "lectin" as used herein refers to any molecules including proteins, natural or genetically modified, that interact specifically with saccharides (ie. carbohydrates). While the examples herein refer to a natural plant lectin, the term "lectin" herein refers to lectins from any species, including but not limited to plants, animals, insects and microorganisms, having a desired carbohydrate binding specificity. Examples of plant lectins include, but are not limited to, the Leguminosae lectin family, such as ConA, soybean agglutinin, and lentil lectin. Other examples of plant lectins are the Gramineae and Solanaceae families of lectins. Examples of animal lectins include, but are not limited to, any known lectin of the major groups S-type lectins, C-type lectins, P-type lectins, and I-type lectins.

The term "SPR" as used herein refers to a surface plasmon resonance. Any SPR device can be used in the present invention including, but not limited to, a Biocore system (GE Healthcare) or the SPR biosensor device as described in U.S. patent application Ser. No. 11/581,260 to Xiao and Zeng, filed Oct. 10, 2006.

The term "QCM" as used herein refers to a quartz crystal microbalance. Any quartz crystal microbalance devices can be used in the present invention including, but not limited to QCM devices available from Maxtek Inc. of Santa Fe Springs, Calif. Other QCM devices which can be used in the present invention are described in U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al., U.S. Pat. No. 6,890,486 to Penelle, U.S. Pat. No. 6,848,299 to Paul et al., U.S. Pat. No. 6,706,977 to Cain et al., U.S. Pat. No. 6,647,764 to Paul et al., U.S. Pat. No. 6,492,601 to Cain et al., U.S. Pat. No. 6,439,765 to Smith, U.S. Pat. No. 6,190,035 to Smith, U.S. Pat. No. 6,106,149 to Smith, U.S. Pat. No. 5,885,402 to Esquibel, U.S. Pat. No. 5,795,993 to Pfeifer et al., U.S. Pat. No. 5,706,840 to Schneider, U.S. Pat. No. 5,616,827 to Simmermon et al., U.S. Pat. No. 5,484,626 to Storjohann et al., U.S. Pat. No. 5,282,925 to Jeng et al., U.S. Pat. No. 5,233,261 to Wajid, U.S. Pat. No. 5,201,215 to Granstaff et al., U.S. Pat. No. 4,999,284 to Ward et al., and U.S. Pat. No. 4,788,466 to Paul et al. Examples of control circuitry for quartz crystal microbalances and methods for detecting materials using piezoelectric resonators are described in U.S. Pat. No. 5,117,192 to Hurd and U.S. Pat. No. 5,932,953 to Drees et al. Each of the above references are hereby incorporated herein by reference in their entirety.

Carbohydrates cover cell surfaces and the interaction of carbohydrates with their surrounding environment is one of the most fundamental molecular recognition events. The interaction of carbohydrates (also called ligands or epitopes) with their corresponding proteins (also called receptors) involves in cell/cell recognition, invasion of virus/bacteria/toxins, antibody recognition, hormonal action and many other physiological and pathological processes. Therefore, carbohydrate ligands or epitopes in principle can be used as sensing elements to detect and monitor a variety of recognition events.

A high percentage of harmful bacteria and their secreted toxins bind specific carbohydrate sequences on the surface of human cells at the initial recognition and attachment site. Recently it has become clear that type 1 fimbriae present on the surface of Enterobacteriaceae are responsible for mannose- and mannoside-binding activity. *Escherichia coli* (*E. coli*), especially *E. coli* 0157:H7 is a significant cause of food contamination and food-borne illness. Preventing food contamination from *E. coli* requires effective risk management controls at all stages of the food production continuum. Proper hygiene and controls must be incorporated into all processes, from agricultural production to final preparation and serving. In order to fulfill this requirement the development of systems for quick, one-step detection of *E. coli* and other harmful microorganisms is crucial.

Knowing the nature of bacteria and their host cell invasion processes, where carbohydrate interactions play an important role in the stability and rigidity of saccharide assemblies, it seems logical to use carbohydrate structures as receptor elements in pathogen detection schemes.

However, carbohydrate-protein interactions are often weaker than protein-protein interactions, by perhaps a factor of $10^2$-$10^3$ based on typical antibody equilibrium dissociation constants ($K_D$). Additionally, it is commonly accepted that apart from toxins and bacteria, many other endogenous and exogenous proteins could recognize the carbohydrate ligand, which could lead to high cross activity. The important question is whether these prevalent interactions could provide a suitable alternative to the use of antibodies or nucleic acid for detection and identification.

There are few examples to-date of carbohydrates actually being employed in biological detection systems. Ganglioside-bearing liposomes have been used for the identification and differentiation of cholera toxin, botulinum toxin C fragment, and tetanus toxin C fragment, for which sensitivity was as low as 1 nM. Detection of cholera toxin by $G_{M1}$ ganglioside recognition has also been investigated using flow cytometry, and fluorescence self-quenching as a signal-transduction mechanism, with sensitivities of 10 and 50 pM, respectively. A biosensor based on detection of the disaccharide Gal($\alpha$1-4)Gal, has been used for identification of uropathogenic p-fimbriated *E. coli*, while influenza virus has been detected calorimetrically with glycopolythiophenes containing sialic acid. Overall, the examples above show that the carbohydrate ligands or epitopes in principle have the potential to act as sensing elements to detect a variety of recognition events which can lead to early detection for cell invasion, tissue destruction and system infection. However, up to now, the optimal conditions for their application as receptor elements, particularly when a non-labeled transducer is selected as the transduction mechanism, have yet to be developed.

A non-label biosensor such as Quartz Crystal Microbalance (QCM) or Surface Plasmon Resonance (SPR) offers significant advantages over current labeled techniques. Being label free, it dispenses with the time and cost demanding labeling step, and also eliminates any possible interference of the "true" binding process due to the presence of the labels. As such, our method allows the analysis of real time interactions of any biomolecule and is able to deliver high quality, high information content analysis for complicated biological recognition processes. Commercial developments of such techniques have been slow mostly due to a failure to appreciate the scale of the analytical problems and the inconsistent results sometimes obtained.

QCM is a mass sensor and is ideal for detecting analytes of high molecular weights. It gives a response that characterizes the binding event between the analyte to be detected and a sensing layer, which is immobilized on the surface of the QCM transducer. The resonant QCM frequency depends on the mass attached to the quartz crystal surface according to the Sauerbrey relationship, $\Delta f = -2\Delta m n f_0^2/[A(\mu_q \rho_q)^{1/2}]$, where n is the overtone number, $\mu_q$ is the shear modulus of the quartz ($2.947 \times 10^{11}$ g/(cm·sec$^2$), and $\rho_q$ is the density of the quartz (2.648 g/cm$^3$), which assumes the foreign mass is strongly coupled to the resonator. Methods based on the use of piezoelectric crystal devices have been developed for immunoassays, bacterial detection[1-10] and virus and toxin detection. Due to the non-rigid nature of bacterial cells, researchers are still skeptical about the potential of piezoelectric mass sensing devices for detection of bacteria. QCM measures only those materials that are acoustically coupled to the sensor surface and requires the surface layer to be rigid.[11] Bacterial binding often involves energy dissipation due to internal friction or trapping of water by the cells, which cause damping of the oscillation of the crystals. As a result, surface chemistry needs to be developed to ensure that the bacteria are strongly attached on the QCM transducer surface, which is not a trivial task. For example, in many bacteria, the carbohydrate binding lectins are usually in the form of fimbriae (or pili). The pili typically have a diameter of 3-7 nm and can extend 100-200 nm in length. The bulk of the fimbrial filament is made up of polymers of the major subunit, which thus plays a structural role. Only one of the subunits, usually a minor component of the fimbriae, possesses a carbohydrate combining site and is responsible for the binding activity and sugar specificity of the fimbriae. For example, in type 1 fimbriae, which are made up of hundreds of subunits of four different kinds, the subunit (MW 29-31 KDa) is present in small numbers at intervals along the fimbrial filament and at the distal tip. However, only these subunits appear to be able to mediate mannose-sensitive adhesive interactions, whereas the subunits at the other positions are inaccessible to the ligand. Consequently, binding is generally of low affinity and not rigid. But since the adhesions and the receptors often cluster in the plane of the membrane, the resulting strength of the interaction can be quite strong.

Bacteria cells have rigid cell wall so they are more rigid than eukaryotic cells. Additionally, the cell wall composes of polysaccharides and peptides, for example lipopolysaccharides (LPS), which are often unique to specific bacterial strains (i.e. sub-species) and are responsible for many of the antigenic properties of these strains. LPS consist of a hydrophobic domain known as Lipid A anchored in the membrane, a "core" oligosaccharide, and a polysaccharide (O-antigen). The O-antigens, being at the utmost cell surface, are at the interface between the bacterium and its environment, and are important virulence factors and antigens for many pathogenic bacteria. Many bacteria are sub-classified by the O-antigen on their surface. For example, E. coli has 166 different O-antigens reported so far. The surface polysaccharide structures of several other bacteria have also been structurally defined. Therefore, LPS of gram-negative bacteria is the most striking character for bacteria providing the selective specificity needed for the lectin recognition.

A completely new approach has been developed that uses both the selective lectin-O-antigen recognition and carbohydrate-protein recognition for bacterial detection that provides enhanced specificity and needed rigidity for non-label QCM biosensors. Specifically, a mannose receptor immobilized on the gold QCM sensor surface is used and it is used to detect E. coli W1485 as a model system. As discussed earlier, type-1 fimbriae present on the surface of most E. coli strains are responsible for mannose- and mannoside-binding activity. According to the studies conducted by Otto and coworkers,[10] the direct adhesion of the fimbriated E. coli onto the mannose immobilized QCM surface, is quite flexible, and there might be water layers trapped between the bacteria and QCM surface. This non-rigid binding may cause damping of the oscillation. Given the fact that E. coli and other bacteria especially the gram-negative bacteria, have chemically distinct surface lipopolysaccharides (LPS) that could be recognized by specific lectins, Concanavalin A (Con A) is preferably first bound to the E. coli W1485. ConA, isolated from Jack bean (*Canavalia ensiformis*) is the most widely used and well-characterized mannose binding lectin. Con A can aggregate on specific terminal carbohydrates of bacterial surface LPS with different binding ability. The multivalent binding of Con A to the E. coli surface receptor favors the strong adhesion of E. coli to mannose immobilized on the QCM surface. As a result, Con A increases the contact area between the E. coli cell and the mannose ligands immobilized on the gold QCM surface. This leads to a relatively rigid and strong attachment that enhances and amplifies the binding between E. coli and the mannose receptor (see FIG. 1). Our approach not only overcomes the challenges of applying QCM technology for bacterial detection but also increases the binding of bacteria to their carbohydrate receptor through bacterial surface binding lectins, thus significantly enhanced specificity and sensitivity of QCM biosensors.

Additionally, the advantage of SAM and the synthetic strength of molecular design here combined by building a functional mannose coating to prevent non-specific adsorption. The linker for the functional mannose coating consists of two parts: the polyethylene glycol ([OCH$_2$CH$_2$]$_n$OH, n=4) portion and the saturated alkyl portion (R=(CH$_2$)$_{11}$) (FIG. 1). The polyethylene glycol part is linked with mannose, while the alkyl portion is terminated with —SH group, which will anchor the molecule on the Au surface of the QCM or SPR sensor. mPEG-thiol was used as a blocking reagent to reduce the nonspecific adsorption. Previous research shows that monolayers terminated in short oligomers of the ethylene glycol group ([OCH$_2$CH$_2$]$_n$OH, n=3-6) prevent the adsorption of proteins under a wide range of conditions.[12] This alternative approach has several advantages over current methods including well-defined surface chemistry, relative stability and facile formation into defined supramicron to nanometer-scale two-dimensional patterns.

Materials and Methods.

Chemicals and Materials: 1H and $^{13}$C NMR spectra were recorded on a VXR400 NMR and a Varian Unity 500 MHz spectrometers. Mass spectra were run on Kratos MS-80 and Kratos MS-50 instruments. Thin-layer chromatography was conducted on precoated Whatman K6F silica gel 60 Å TLC plates with a fluorescent indicator. EM Science silica gel 60 Geduran (230-400 Mesh) was used for column chromatography. Concanavalin A (Con A), and lectin from *Erythrina cristagelli* (ECL) were purchased from Sigma (Sigma-Aldrich, St. Louis, Mo.). *Escherichia coli*, a lambda-derivative of *E. coli* strain W1485 (ATCC® 12435™) was obtained from ATCC. mPEG-thiol was purchased from NEKTAR. Phosphate buffered saline and fetal bovine serum were obtained from Gibco.

Bacterial strain and culture: The pure culture of *Escherichia coli*, a lambda-derivative of *E. coli* strain W1485 (ATCC® 12435™) was grown in ATCC®294 broth (tryptone with NaCl) at 37° C. for 24 hr in a shaking incubator. The viable cell number was determined by conventional agar plate counting.

Phosphorus tribromide (5.3 g, 19.6 mmol, 1.84 ml) was added dropwise to a solution of 10-Undecen-1-ol (10 g, 58.7 mmol) in diethyl ether (100 ml) at −78° C. over a period of 10 min and then the mixture was allowed to warm to room temperature and stirred under Ar overnight. The reaction mixture was quenched with water and the layers were separated. The aqueous layer was extracted with ether (5×30 ml) and the combined organic layers were washed with brine and dried over sodium sulfate. After evaporation of the solvent in vacuo, the crude product was purified by chromatography column on silica gel (hexane) to give pure product 8.2 g (yield: 60%). $^1$H NMR (CDCl$_3$) δ 5.85-5.75 (m, 1H), 5.01-4.91 (m, 2H), 3.37-3.41 (t, 2H, J=7.2 Hz), 2.06-1.99 (m, 2H), 1.88-1.81 (m, 2H), 1.39 (br, 2H), 1.29 (br, 10H). $^{13}$C NMR (CDCl$_3$) δ 139.4, 114.3.3, 34.2, 34.1, 33.0, 31.8, 29.6, 29.3, 29.1, 29.0, 28.4.

A mixture of 1 ml of 50% aqueous sodium hydroxide (0.012 mol) and 23.4 g of tetra (ethylene glycol) (0.12 mol) was stirred for 0.5 h in an oil bath at 100° C. under Ar, and 2.8 g of 11-bromoundec-1-ene (0.012 mol) was then added. At the completion of the reaction as indicated by the TLC analysis, the reaction mixture was cooled and extracted several times with hexane. The combined organic layers were washed with brine and dried over sodium sulfate. After evaporation of the solvent in vacuo, the crude product was purified by chromatography column on silica gel (hexane/ethyl acetate, 1:1) to give pure product 2.5 g (yield: 60%). $^1$H NMR (CDCl$_3$) δ 5.82-5.72 (m, 1H), 4.97-4.87 (m, 2H), 3.68-3.64 (t, 2H, J=4.8 Hz), 3.62-3.54 (m, 14H), 3.42-3.39 (t, 2H, J=7.2 Hz), 2.01-1.97 (m, 3H), 1.55-1.50 (m, 2H), 1.35-1.24 (m, 12H). $^{13}$C NMR (CDCl$_3$) δ 139.5, 114.4, 72.8, 71.8, 70.8, 70.7, 70.5, 70.2, 34.0, 29.8, 29.7, 29.6, 29.3, 29.1, 26.3. MS ES$^+$ m/z 369.28 (M+Na).

Solutions of Undec-1-en-11-yltetra (ethylene glycol) (2.66 g, 7.7 mmol) in MeOH (40 ml) containing 3 equivalent of thioacetic acid (1.6 ml) and 5 mg AIBN were purged with Ar for one hour (1 h), then the mixture was irradiated under standard conditions (medium pressure mercury lamp, Pyrex glass filter) until the disappearance of the starting materials as indicated by TLC analysis. At the completion of the reaction, the solvent was removed in vacuo, the crude product was purified by chromatography on silica gel (hexane/ethyl acetate 2:1) to give pure product 2.3 g (yield: 70%). $^1$H NMR (CDCl$_3$) δ 3.62-3.46 (m, 16H), 3.36-3.33 (t, 2H, J=6.4 Hz), 2.77-2.73 (t, 2H, J=7.2 Hz), 2.21 (s, 3H), 2.19 (m, 2H), 1.49-1.44 (m, 2H), 1.16 (br, 14H). $^{13}$C NMR (CDCl$_3$) δ 196.1, 72.8, 71.7, 70.7, 70.4. 70.1, 61.7, 30.7, 29.7, 29.6, 29.5, 29.2, 28.9, 26.2. MS ES$^+$ m/z 445.34 (M+Na).

Linker [1-[(Methylcarbonyl)thio]undec-11-yl]-tetra(ethylene glycol) (0.889 g, 2.1 mmol) in 20 ml anhydrous dichloromethane, HgBr$_2$ (0.94 g, 2.4 mmol) and Hg(CN)$_2$ (0.65 g, 2.4 mmol) were added to a previously flame-dried flask containing 1 g 4 Å molecular sieve. After the mixture was stirred for one hour (1 h) under Ar, 2,3,4,6-tetra-O-acetyl-α-D-mannosyl bromide (1.25 g, 2.94 mmol) was added to the mixture. The mixture was stirred in the dark at ambient temperature until the completion of the reaction as indicated by TLC analysis. The resulting mixture was passed through a Celite packed glass funnel, and washed with saturated NaHCO$_3$ and brine. The organic phase was dried over anhydrous Na$_2$SO$_4$ and concentrated in vacuo. The resulting residue was purified by chromatography column on silica gel (hexane/ethyl acetate, 1:1) to give the product 0.96 g (yield: 61%). $^1$H NMR (CDCl$_3$) δ 5.30-4.80 (m, 3H), 4.68 (br, 1H), 4.11-4.05 (m, 1H), 3.93-3.88 (m, 2H), 3.68-3.37 (m, 16H), 3.24 (t, 2H, J=7.2 Hz), 2.67-2.64 (t, 2H, J=6.8 Hz), 2.12 (s, 3H), 1.95 (s, 3H), 1.90 (s, 3H), 1.85 (s, 3H), 1.84 (br, 2H), 1.78 (s, 3H), 1.36 (br, 2H), 1.07 (br, 14H). $^{13}$C NMR (CDCl$_3$) δ 195.7, 170.5, 169.9, 97.7, 71.4, 70.5, 70.0, 69.5, 69.1, 68.4, 67.3, 66.1, 62.7, 62.4, 60.3, 29.6, 29.5, 29.4, 28.7, 20.8. MS ES$^+$ m/z 775.47 (M+Na).

Anhydrous methanol (MeOH) was added to [1-(Methylcarbonyl)thio]undec-11-tetra(ethylene glycol) 2,3,4,6-tetra-O-acetyl-α-D-mannopyranoside (0.814 g, 1.08 mmol). After the solution was flushed with argon (Ar) for 20 min., NaOMe (0.583 g, 10.8 mmol) was added, the reaction mixture was stirred under Ar at room temperature (r.t.) until the completion of the reaction as indicated by the TLC analysis. Dowex cation exchange resin (H form) was added to adjust the pH to 6-7, the resin was filtered off and the filtrate was concentrated in vacuo. The resulting residue was purified by chromatography (CH$_2$Cl$_2$/MeOH, 5:1) to afford the product (8) 526 mg (yield: 90%). $^1$H NMR (CD$_3$OD) δ 4.79 (d, J=1.8 Hz, 1H), 3.84 (dd, J=4.0 Hz, 1H), 3.80-3.81 (m, 2H), 3.72 (m, 1H), 3.71 (d, J=13.2, 2H), δ 3.65-3.64 (m, 16H), 3.36-3.33 (t, 2H, J=6.4 Hz), 2.77-2.73 (t, 2H, J=7.2 Hz), 2.21 (s, 3H), 2.19 (m, 2H), 1.49-1.44 (m, 2H), 1.16 (br, 14H) $^{13}$C NMR (CD$_3$OD) δ 100.5, 73.4, 70.4, 70.2, 69.9, 67.4, 66.6, 61.7, 34.1, 29.5, 29.1, 28.3, 26.0, 23.8. ESI m/z 541.48.

Quartz Crystal Microbalance: A non-polished gold quartz crystal (International Crystal Manufacturing Co. Inc.) was mounted in a (custom-made Kel-F cell [please detail]). It was cleaned three times using a mixture of concentrated nitric acid and sulfuric acid (1:1 v/v), biograde water and ethanol in series, and then the cell was dried using a nitrogen stream. The frequency of the electrode was measured in PBS (pH 7.2). One side of the gold quartz crystal was incubated in a solution of 4 mg/ml mannose thiol linker conjugate in anhydrous ethanol at 4° C. overnight. After incubation, the gold surface was washed with ethanol and biograde water and then dried under nitrogen to give mannose SAMs. Any remaining sites on the mannose modified QCM surface were blocked using 3 mg/ml mPEG-thiol (PI-03D-18, NEKTAR) for 6 hr. The changes in frequency and damping resistance of the QCM were monitored simultaneously using a network/spectrum/impedance analyzer (Agilent 4395A) controlled by a PC via an Intel card.

Surface Plasmon Resonance: A surface plasmon resonance (SPR) biosensor was used to detect bacterial attachment. The light source was a 06-DAL-103 model semiconductor diode laser (Melles Griot Inc., California) with 4 mW power output, as described in U.S. patent application Ser. No. 11/581,260 to Xiao and Zeng, filed Oct. 10, 2006, incorporated herein by reference in its entirety. The wavelength of the polarized laser was 650 nm. The refractive index of the glass prism (ZF7)

used is 1.79. A series-600 angular sensor (Trans-Tek Inc., Ellington, Conn.) is used to measure laser incident angles. With a fifteen volt direct current (15V DC) input, the capacitance angle sensor can give an angle signal output of 100 mV/Degree. Also a solar cell is used to convert reflected light intensity into electric voltage. The two analog signals from the angular sensor and the solar cell are converted into 16-bit digital signals by an USB-1608FS data acquisition module (Measurement Computing Corporation, MA), which is connected to a PC through a USB cable. The hardware of the SPR biosensor is controlled by a program written in Labview® 8.0.

Results and Discussion

Figure 2:
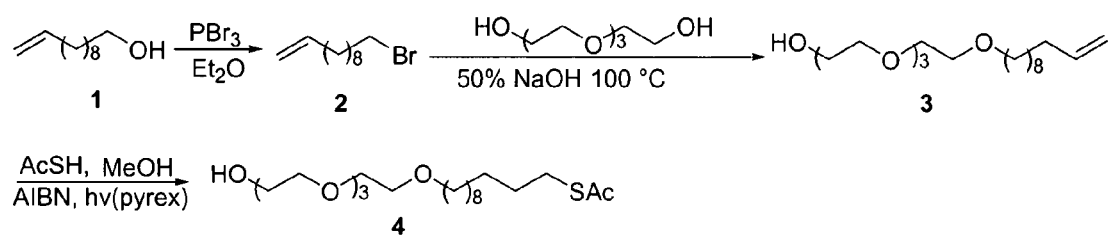
FIG. 2 is a scheme illustrating the synthesis of linker [1-[(Methylcarbonyl)thio]undec-11-yl]-tetra(ethylene glycol).
Figure 3:
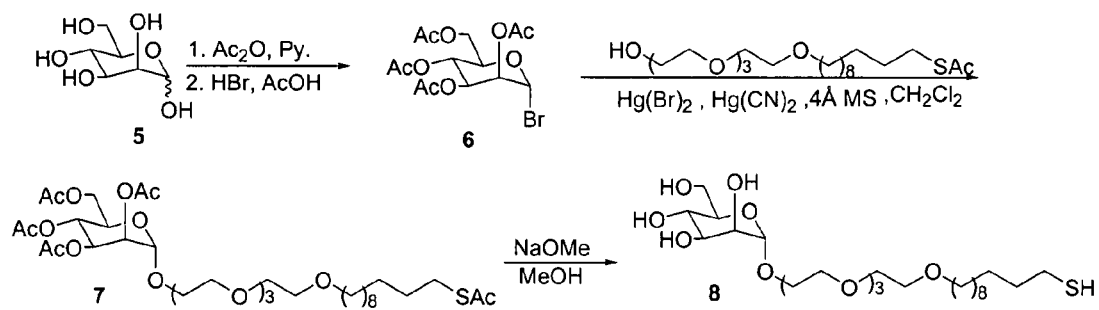
FIG. 3 is a scheme illustrating the synthesis of (1-Mercaptoundec-11-yl) tetra (ethylene glycol) D-mannopyranoside conjugate.

Synthesis: Synthesis of linker [1-[(Methylcarbonyl)thio] undec-11-yl]-tetra(ethylene glycol) is shown in FIG. 2. Treatment of the commercially available ω-undecylenyl alcohol with $PBr_3$ and then reaction with tetraethylene glycol gives undec-1-en-11-yl tetra-(ethyleneglycol) (3), which is then treated with thiolacetic acid under photolysis condition initiated by AIBN to provide the desired linker [1-[(methylcarbonyl) thiol] undec-11-tetra(ethylene glycol) (4). The synthesis of (1-Mercaptoundec-11-yl) tetra (ethylene glycol) D-mannopyranoside conjugate is shown in FIG. 3. Connection of the linker (4) to mannose via a glycosylation reaction promoted by $HgBr_2$ and $Hg(CN)_2$ and then deprotection provides the target compound (8).

Detection of Con A by mannose-QCM: Con A has identical subunits of 237 amino acid residues (M.W.: 26,000). At neutral pH, Con A is predominantly tetrameric with optimal activity. At pH 4.5-5.6, Con A exists as a single dimer. Two metal ions ($Mn^{2+}$ and $Ca^{2+}$) can bind to Con A; both must be present for carbohydrate binding. Therefore, Con A has been used to examine the mannose-QCM sensor performance.

Figure 4:
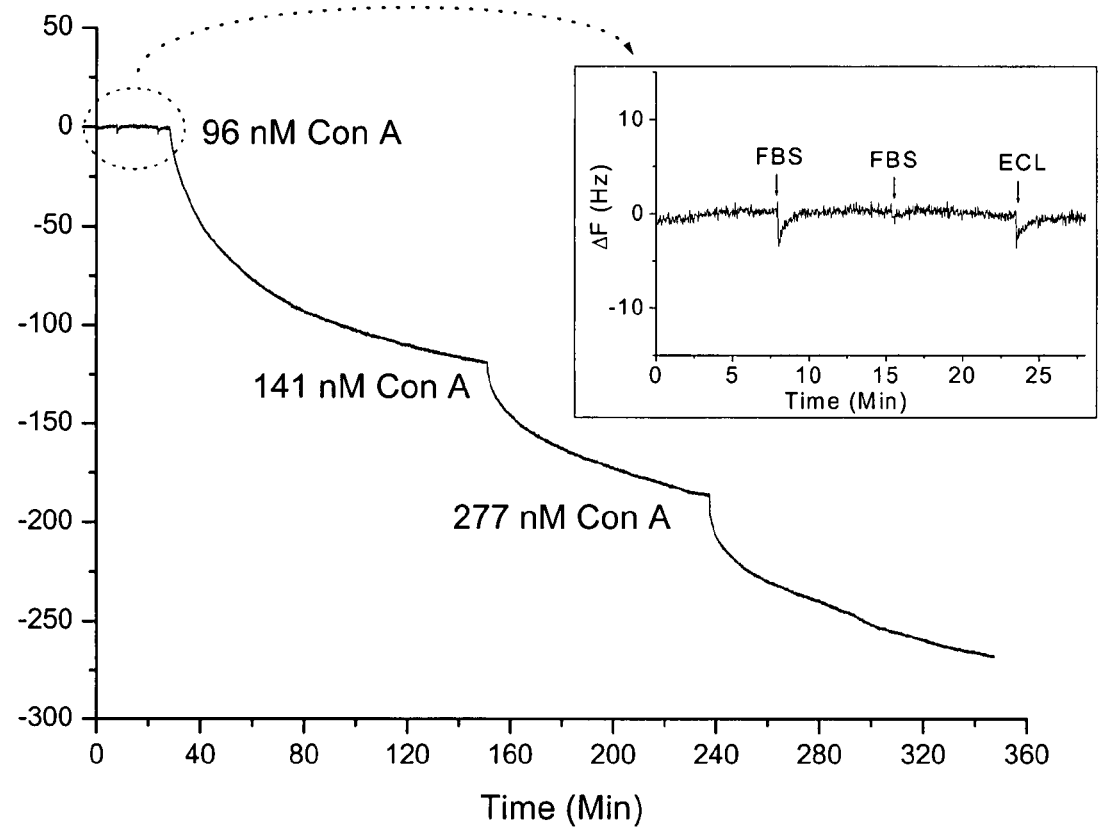
FIG. 4 is a graph of the frequency change vs. time curve when FBS (5.2 μg/ml), ECL (142 nM) and different concentrations of Con A solutions were added sequentially to the mannose-QCM in 1.0 ml PBS buffer (pH=7.2) with 1 mM $Mn^{2+}$ and 1 mM $Ca^{2+}$.

To examine our mannose sensor's specificity, *erythrina cristagalli* lectin (ECL), a galactose-specific legume lectin, was used as a negative control. Fetal bovine serum (FBS), the most widely used serum in the culturing of cells, tissues and organs, was also selected as a negative control. As shown in FIG. 4 Insertion, there were negligible frequency changes for the addition of FBS and ECL. This result shows that the mannose-QCM sensor is antigen specific. After exposure to FBS and ECL, Con A at different concentrations was consecutively added to the sensor (FIG. 4). This study demonstrates that the mannose-QCM sensor has high sensitivity and specificity for binding with the Con A even after exposure of the sensor surface in a complex matrix (i.e. FBS and ECL).

The apparent binding affinity for Con A binding to the mannose QCM surface was estimated by using the Langmuir adsorption model. According to the following equation (Equation 1), the mass change at equilibrium was related to the original concentration of Con A.

$$[ConA] + [\text{mannose epitopes}] \underset{k_2}{\overset{k_1}{\rightleftarrows}} [ConA - \text{mannose complex}] \quad \text{Equation 1}$$

$$Ka = \frac{k_1}{k_2}$$

$$\frac{[Con\,A]}{\Delta M} = \frac{[Con\,A]}{\Delta M_{max}} + \frac{1}{\Delta M_{max} K_A}$$

In Equation 1, $\Delta M_{max}$ is the maximum binding amount, $\Delta M$ is the measured binding amount at equilibrium, and [Con A] is the original concentration of Con A.

The value of $K_A$ for the binding between Con A and mannose was estimated to be $(5.6\pm1.4)\times10^6$ $M^{-1}$ (n=5). This result is in good agreement with reported literature values [$(5.6\pm1.7)\times10^6$ $M^{-1}$][13] and our previous work [$(8.7\pm2.8)\times10^5$ $M^{-1}$ (QCM), $(3.9\pm0.2)\times10^6$ $M^{-1}$ (SPR)].

Figure 5:
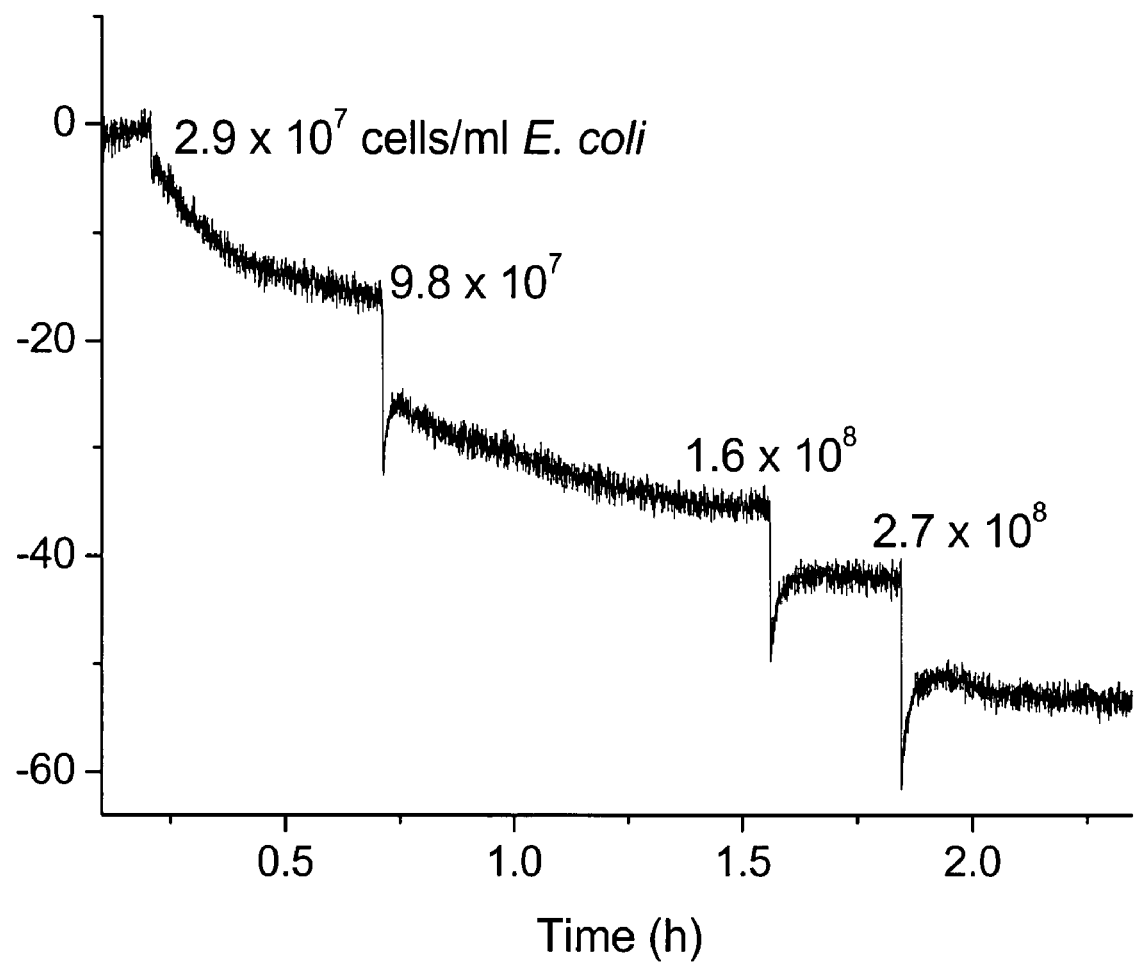
FIG. 5 is a graph of the frequency change vs. time curve when the mannose-QCM electrode was exposed to different concentrations of *E. coli* W1485 ($2.9 \times 10^7$, $9.8 \times 10^7$, $1.6 \times 10^8$, and $2.7 \times 10^8$ cells/ml) in 1.0 ml stirred PBS buffer (pH=7.2) with 1 mM $Ca^{2+}$ and 1 mM $Mn^{2+}$.

(2) Detection of *E. coli* W1485 by mannose-QCM: *E. coli* W1485 (ATCC® 12435™) carries type 1 fimbriae, which is specific for mannose binding. The *E. coli* cell is about a million times heavier than Con A and typical antibodies; theoretically the binding between *E. coli* and mannose receptor on the QCM surface should lead to a very large response. However, when the mannose modified QCM electrode was exposed to the different concentrations of *E. coli* W1485 ($2.9\times10^7$, $9.8\times10^7$, $1.6\times10^8$, and $2.7\times10^8$ cells/ml), only small signals were observed (FIG. 5). The linear range is very narrow narrow (i.e. $2.9\times10^7$-$2.7\times10^8$ cells/ml). The following explanations have been suggested for this unexpected phenomenon. First, the fimbriae mediated adhesion is relatively weak and flexible. Along with the high mobility of the bacteria, it created large freedom of movement of the bacteria on the QCM surface. This non-acoustic attachment cannot be easily measured by QCM technique. Secondly, QCM will give a signal only if the above interaction results in a net change of mass. The weak and flexible binding of the fimbriae to the mannose may result in a displacement of one species with another.

Consequently, the surface is only a temporary host to the *E. coli* and the net change of mass is very small. Finally, a major issue which must be considered in bacterial detection is that of antigenic or phase variation. Phase variation is the adaptive process by which bacteria undergo frequent and reversible phenotypic changes as a result of genetic alterations in specific loci of their genomes. This process is crucial for the survival of pathogens in hostile and ever-changing host environments. As a result, type 1 *E. coli* bacteria might shift from a fimbriated phase to a nonfimbriated phase and back spontaneously, which might affect the fimbriated *E. coli* attachment.

(3) Detection of *E. coli* W1485 by mannose/lectin-QCM: As pointed out by E. V. Olsen, et. al., a piezoelectric mass sensor will not be able to provide quantitative information for bacterial detection if binding of bacteria on the sensor surface is neither predominantly rigid nor predominantly flexible. The key is to ensure adequate bacterial binding by using recognition molecules with high affinity and multiple binding valences. Here we take advantage of the fact that bacteria and fungi have chemically distinct surface polysaccharide carbohydrate structures that can be recognized by lectins in agglutination studies. We used lectin Con A as an *E. coli* adhesion promoter to strongly attach *E. coli* to the mannose so a rigid binding layer would be formed on the QCM surface (FIG. 1).

In order to prove the above strategy, experimental conditions need to be selected so that we can unquestionably demonstrate that the Con A adsorbed on the *E. coli* cell surface facilitates the binding of *E. coli* to the mannose receptor rather than free Con A in the mixture of bacteria and Con A binding to the mannose receptor. The mannose modified QCM surface was immersed in a 100 nM Con A solution for 2 h, then the electrode was rinsed with PBS buffer to remove the unbounded Con A and the cell was refilled with fresh PBS buffer containing 1 mM $Ca^{2+}$ and $Mn^{2+}$. When the similar concentration of *E. coli* W1485 was added to the test chamber in which the mannose modified QCM surface has preadsorbed Con A but no Con A is in the binding solution, only ~40 Hz frequency shift was observed which is much smaller than the 250 Hz signal obtained when ConA is also present in the solution phase. Similar results were obtained by SPR experiments (data not shown). Both study confirmed that the agglutination of Con A to the *E. coli* in solution phase is the key reason for the signal amplification.

We further studied two experimental conditions. In one, a low concentration of Con A was first added to the mannose sensor test chamber. The concentration of Con A added is relatively small so that the mannose surface is not saturated still room to reduce it further. Additionally, as evident from the Sauerbrey equation above, the sensitivity of the QCM sensor increases with the square of $f_0$ and linearly with n; thus by working with crystals of higher $f_0$ or at higher harmonics, even higher sensitivity and lower detection limits can be obtained.

TABLE 1

Comparison of QCM biosensors for the detection of *E. coli*

| References | *E. coli* | Assay principle and description | LOD (cells/ml) | Linear ranges (cells/ml) |
| --- | --- | --- | --- | --- |
| (1) | *E. coli* K-12 | Immunosensor: Anti- ECA antibody crosslinked to PEI precoated surface | $10^6$ | $10^6$-$10^9$ |
| (6) | *E. coli* O157:H7 | Immunosensor: Antibody linked to MHDA SAM | $10^3$ | $10^3$-$10^8$ |
| | *E. coli* O157:H7 | DMA sensor: Nanoparticle amplification | $2.67 \times 10^2$ | $2.67 \times 10^2$-$2.67 \times 10^6$ |
| Results of the present invention | *E. coli* W1485 | Carbohydrate sensor (without lectin) | $3.0 \times 10^7$ | $2.9 \times 10^7$-$2.7 \times 10^8$ |
| | *E. coli* W1485 | Carbohydrate/lectin sensor | $7.5 \times 10^2$ | $7.5 \times 10^2$-$7.5 \times 10^7$ |

Figure 6:
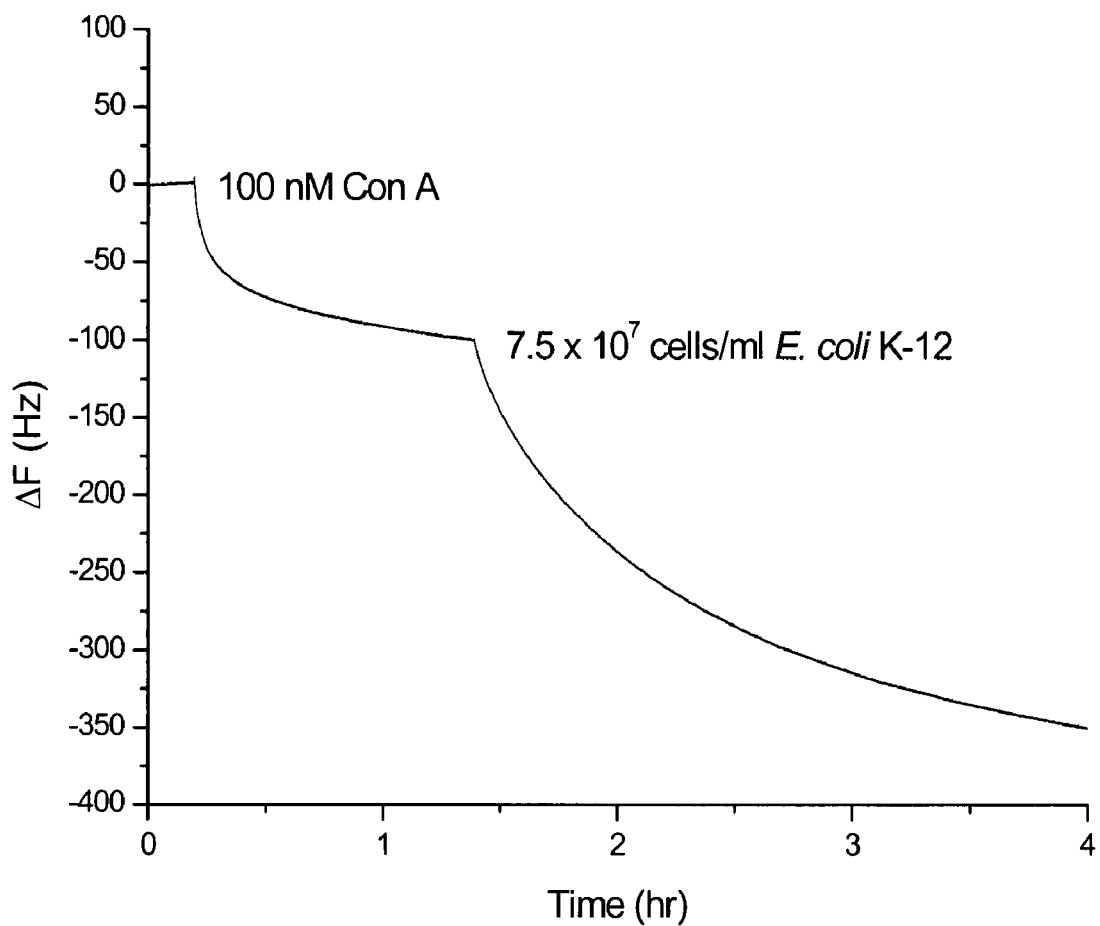
FIG. 6 is a graph of the frequency change vs. time curve when the mannose-QCM sensor was first exposed to 100 nM Con A, followed by the addition of *E. coli* W1485 ($7.5 \times 10^7$ cells/ml) in 1.0 ml stirred PBS buffer (pH=7.2) with 1 mM $Ca^{2+}$ and 1 mM $Mn^{2+}$.

ECA: Enterobacterial common antigen; PEI: polyetheneimine; MHDA: 16-Mercaptohexadecanoic acid; SAM: self-assembled monolayer.

based on the Con A/mannose binding study (FIG. 4) and the surface still has a plethora of available mannose binding sites. When the Con A/mannose binding reached equilibrium, *E. coli* W1485 was added. At this time, small amounts of free Con A in the bulk solution will facilitate the binding of *E. coli* to the mannose receptor as described in FIG. 1. As shown in FIG. 6, the addition of 100 nM Con A to the mannose-QCM generated ~100 Hz frequency change at equilibrium. The subsequent addition of *E. coli* provided a large binding signal (~230 Hz). This result shows that the presence of Con A in the binding solution leads to the signal amplification. Since the interaction between Con A and *E. coli* has already been proved by several studies, we suggest that Con A in the binding solution aggregates on the *E. coli* cell walls through binding to their distinct surface polysaccharide carbohydrate structures that promotes the formation of rigid adhesion onto mannose-QCM.

Figure 7A:
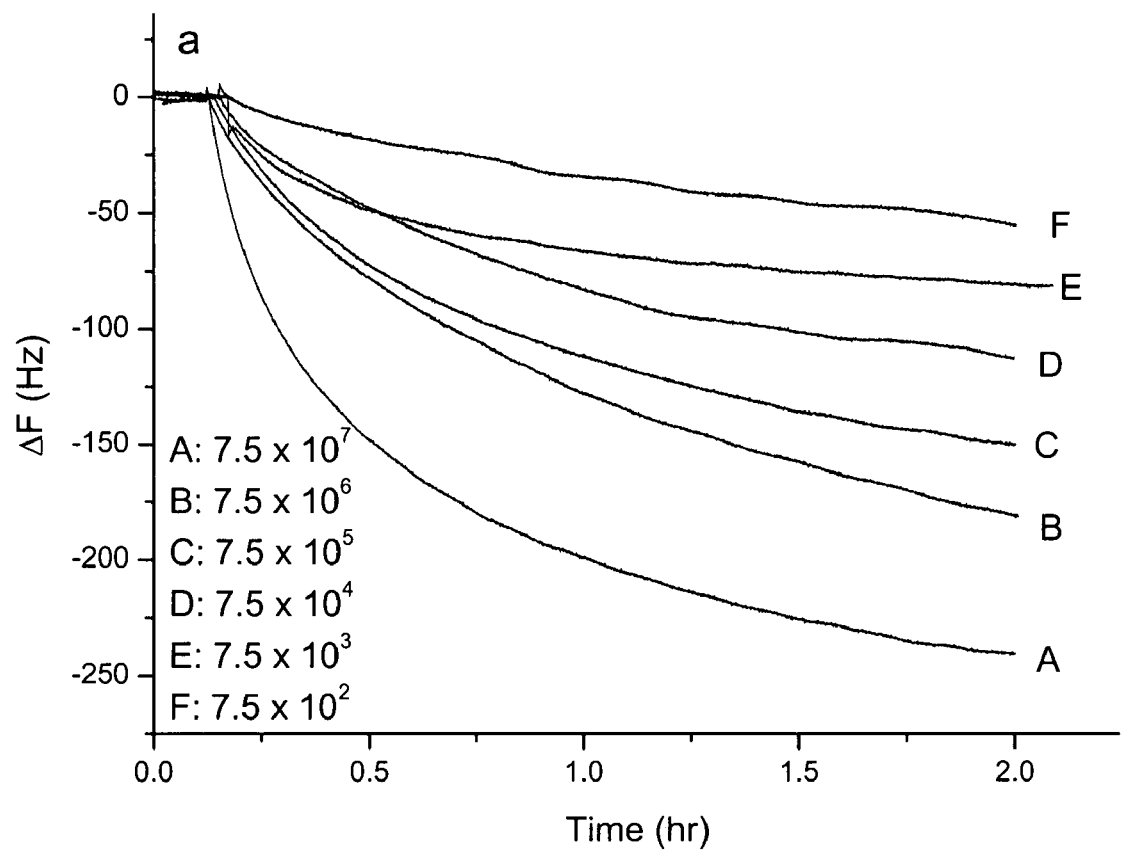
FIG. 7A is the frequency change vs. time curve when mannose-QCM electrodes were exposed to different concentrations of *E. coli* W1485 from $7.5 \times 10^2$ to $7.5 \times 10^7$ cells/ml in 1 ml stirred PBS with 1 mM $Mn^{2+}$ and 1 mM $Ca^{2+}$ and 100 nM Con A. (The mannose-QCM was first exposed to 100 nM Con A solution for about two hours).
Figure 7B:
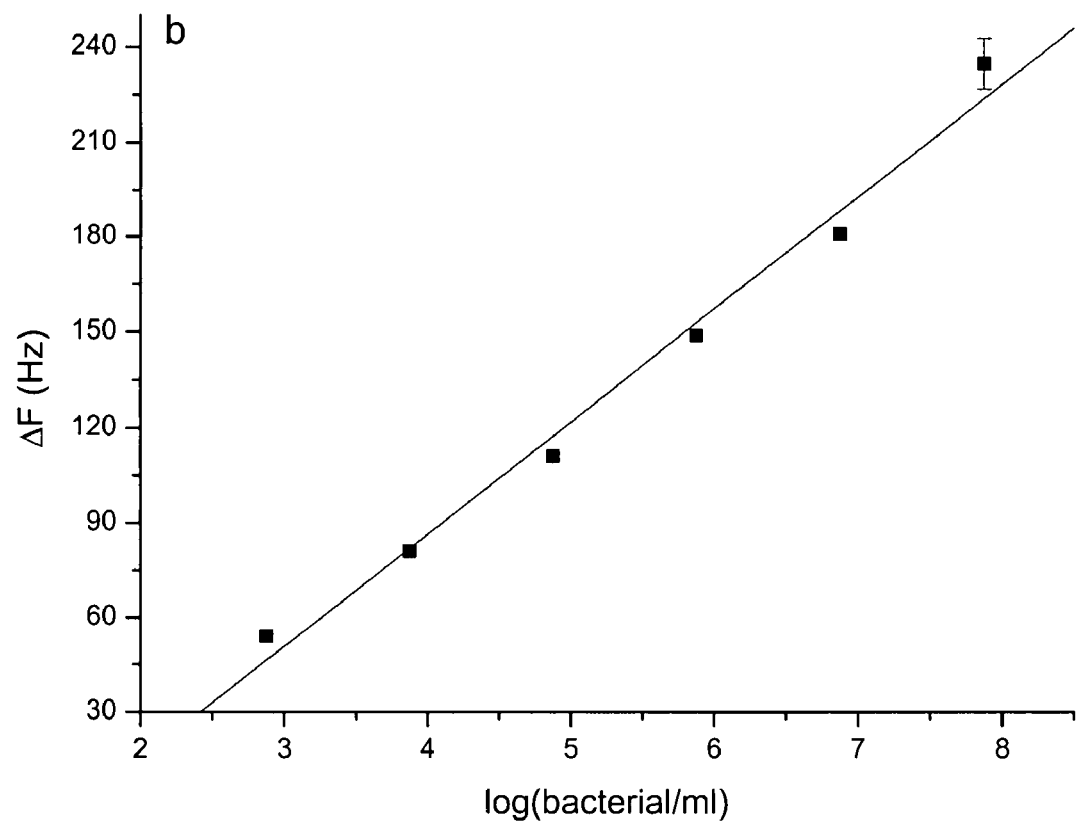
FIG. 7B is a calibration curve showing frequency shift vs. log of *E. coli* concentration.

Sensor sensitivity: The mannose modified QCM surface was first exposed to the 100 nM Con A solution for two hours (2 h) to reach the binding equilibrium, then *E. coli* W1485 samples ranging from $7.5 \times 10^2$ to $7.5 \times 10^7$ cells/ml were injected onto the Con A pretreated mannose-QCM sensor chambers which contain 1 ml PBS with 1 mM $Mn^{2+}$, 1 mM $Ca^{2+}$ and 0.1 mM Con A. Fast and large signal responses were observed. A linear relationship between the frequency shift and logarithm of cell concentration was found from $7.5 \times 10^2$ to $7.5 \times 10^7$ cells/ml (FIG. 7), which is four decades wider than the early mannose alone sensor. The damping resistance in the Butterworth-Van Dyke-equivalent circuit was also determined simultaneously with the frequency shift for the bacterial binding study. The change of damping resistances for *E. coli* adhesion experiments in FIG. 6 and FIG. 7 were no more than 1.4%. This suggests that the bacterial attachment was rigid, rather than a viscoelastic behavior.

Figure 8:
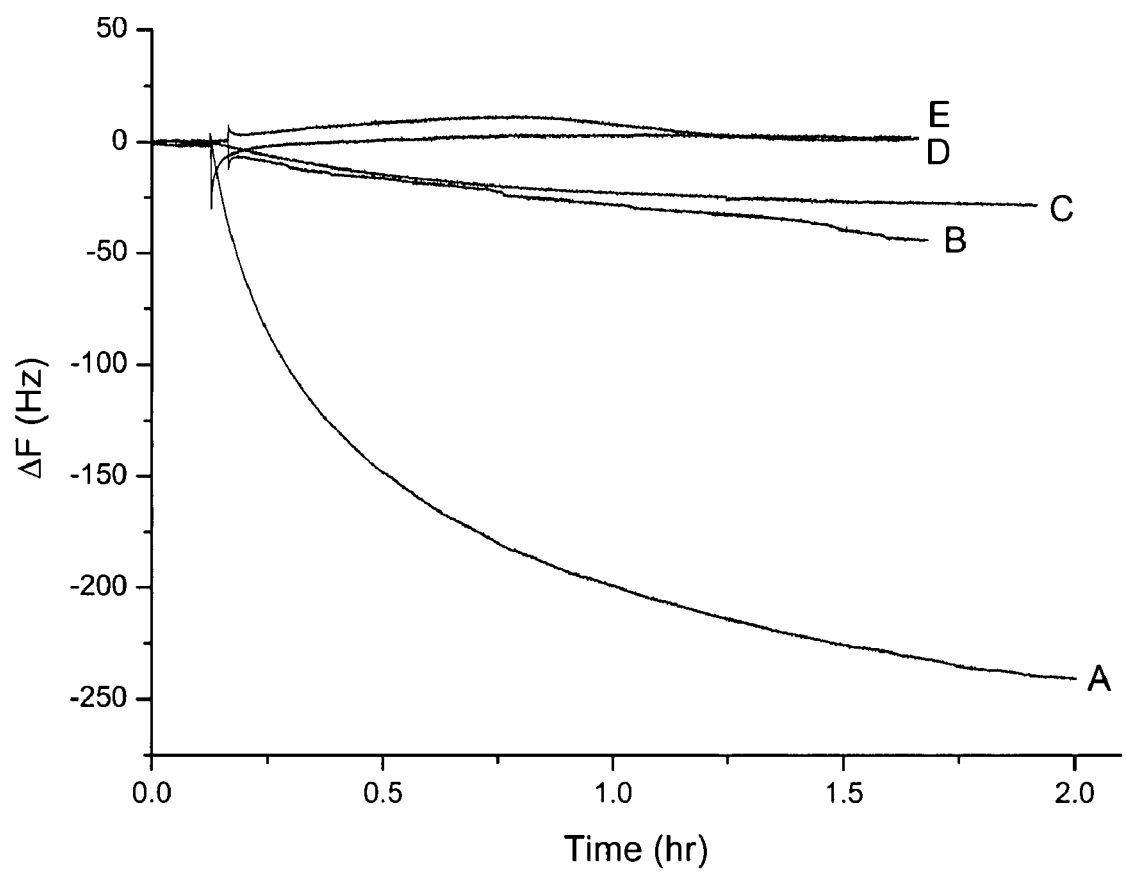
FIG. 8 is a comparison of sensor specificity. Different electrodes were exposed to $7.5 \times 10^7$ cells/ml *E. coli* W1485: A) Con A pretreated mannose electrode with Con A in binding solution; B) Con A pretreated mannose electrode without Con A in binding solution; C) Con A-free mannose surface and Con A-free binding solution; and D) Con A pretreated 210E scFv-cys electrode with Con A in binding solution. E): control antigen: $1.4 \times 10^9$ cells/ml *Staphylococcus aureus* were added to Con A pretreated mannose electrode with Con A in binding solution. All the test chambers contain 1.0 ml stirred PBS buffer (pH=7.2) with 1 mM $Mn^{2+}$ and 1 mM $Ca^{2+}$.

Table 1 lists the limits of detections (LOD) obtained by the QCM technique using antibody or DNA recognition elements as reported in the literature and via the two methods we used (carbohydrate or carbohydrate/lectin recognition elements). Compared to the use of carbohydrate alone, ~$10^4$ fold improvement in detection limits were achieved using lectin amplification. Currently, the combined carbohydrate/lectin detection methods give similar detection limits to DNA sensors using nanoparticle amplification. Since the detection limits in our study are experimentally determined, there is (b) Sensor specificity: Several control experiments were performed to validate the conclusions and to test the sensor specificity. The mannose modified QCM sensor surface was first exposed to 100 nM Con A solution for about two hours (2 h), which allowed Con A to partially occupy the mannose surface activity sites leaving free Con A in the bulk solution. When the Con A/mannose binding reaction reached to the equilibrium, the final concentration of $7.5 \times 10^7$ cells/ml *E. coli* W1485 were added and generated a large signal response (~230 Hz) (FIG. 8, Curve A), which was about 8 times larger than the direct adhesion of *E. coli* W1485 onto the mannose-QCM alone (~30 Hz signal, Curve C). To determine whether the surface bound Con A or the Con A in the binding solution was the major factor for the enhanced *E. coli* W1485 adhesion, the following control experiment was performed. First, the mannose modified QCM surface was immersed in a 100 nM Con A solution for two hours (2 h), then the electrode was rinsed with PBS buffer to remove the unbound Con A and the cell was refilled with fresh PBS buffer containing 1 mM $Ca^{2+}$ and $Mn^{2+}$. When the similar concentration of *E. coli* W1485 was added to the test chamber in which the mannose modified QCM surface has preadsorbed Con A but no Con A is in the binding solution, only ~40 Hz frequency shift was observed (Curve B). This result confirms that the Con A in the binding solution rather than the Con A on the QCM surface played the key role in enhancing *E. coli* cell adhesion onto the mannose modified QCM surface.

A recombinant antibody 210E scFv-cys modified QCM surface was used additionally to exam the specificity of the above system. Recombinant antibody 210E scFv-cys binds specifically to rabbit IgG antigen. With the same experimental condition as FIG. 8 Curve A, negligible frequency change was observed for the addition of *E. coli* W1485 (Curve D).

*Staphylococcus aureus* serotype 1, a gram-positive bacterium, was further used as a negative control. When *Staphylococcus aureus* was added to the Con A pretreated mannose-QCM electrode, only a very small signal was detected (Curve E).

All the above experiments confirmed that Con A in the binding solution aggregated onto the *E. coli* W1485 cell wall thus enhanced the sensitivity and specificity for mannose binding with *E. coli* W1485 by promoting the formation of rigid attachment to the mannose modified QCM surface.

Figure 9:
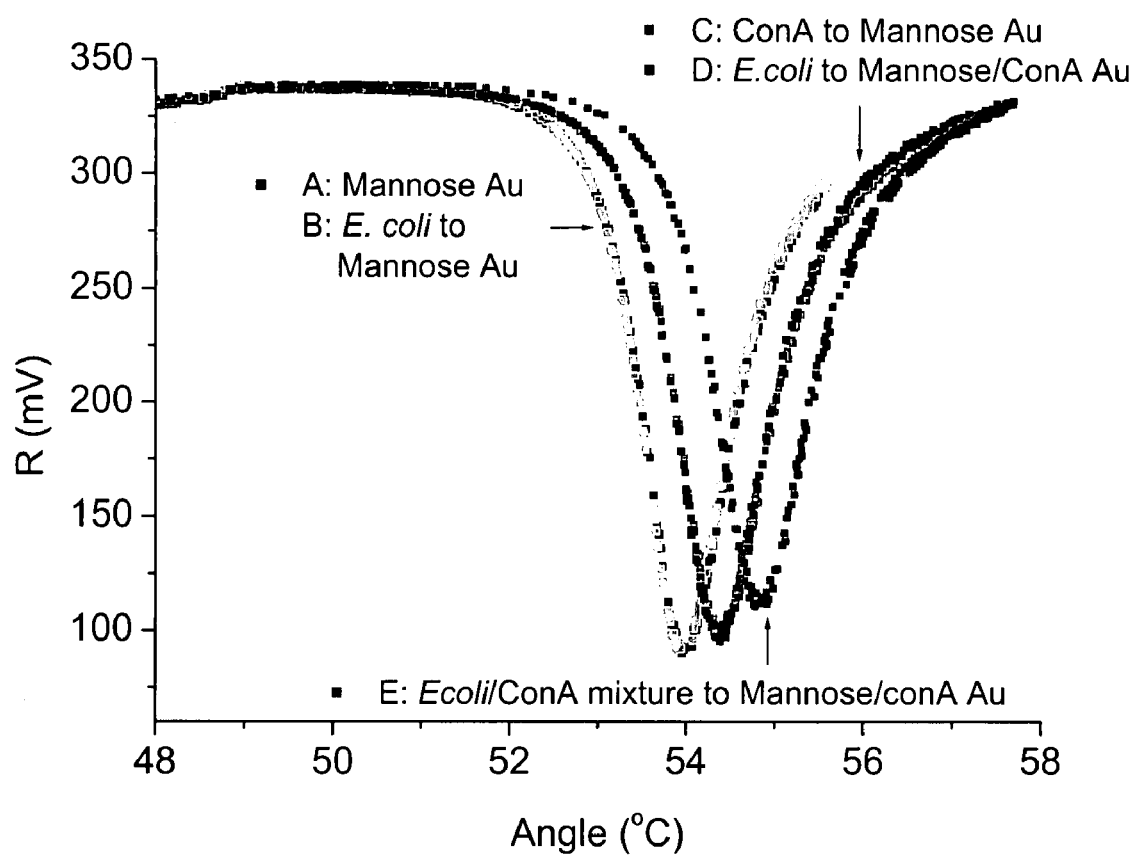
FIG. 9 is an SPR spectrum. A) mannose SAM, B) $3.7 \times 10^8$ cells/ml *E. coli* W1485 was injected into mannose SAM for 60 min, C) 1.25 µM Con injected into mannose SAM for 40 min, D) $3.7 \times 10^8$ cells/ml *E. coli* W1485 was injected to the Mannose/Con A surface for 60 min, E) the mixture of $1.9 \times 10^8$ cells/ml *E. coli* W1485 and 1.25 µM Con A injected to the Con A pretreated Mannose SAM for 70 min.
Figure 9A:
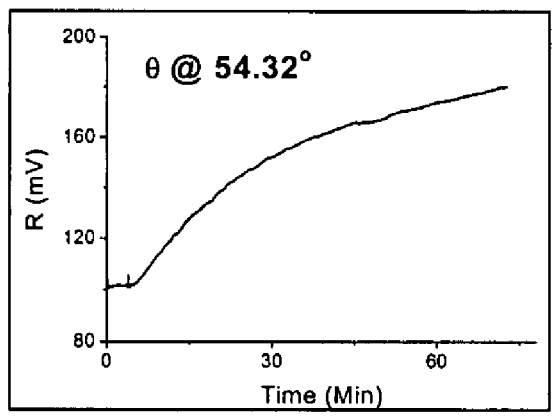
FIG. 9A is the light intensity change with time after the injection of $1.9 \times 10^8$ cells/ml *E. coli* W1485 and 1.25 µM Con A mixture onto the Con A pretreated Mannose SAM. The wavelength of the SPR biosensor light source was 650 nm and the refractive index of its prism was 1.79. The sample chamber of the SPR biosensor was thoroughly washed before recording the spectrum, and filled with 200 µl PBS with 1 mM $Ca^{2+}$, 1 mM $Mn^{2+}$ for each of the experiments.

(c) Validating the mannose/lectin QCM sensor for *E. coli* W1485 detection by a SPR biosensor: Surface plasmon affinity sensors are based on monitoring the changes in the effective refractive index of the guided waves caused by the interactions of their evanescent field with analyte molecules binding specifically to their reaction partners immobilized on the sensor surfaces. Even though SPR spectroscopy and QCM are based on different physical phenomena, it is possible to use SPR to validate our surface chemistry since both techniques are non-label mass sensors and can theoretically provide information for the binding events occurring at solution metal interfaces. FIG. 9 shows the SPR spectra of the stepwise binding of surface receptor to the target analyte. The surface was thoroughly washed after each step and then recorded the spectrum. Little angle shift was observed when *E. coli* W1485 was directly bound to the mannose SAM (Curve B). Con A binds to the mannose surface and leads to 0.41° angle shift (Curve C). However, when *E. coli* W1485 was added to mannose-Con A surface, negligible angle shift was observed (Curve D) confirming our early rational that the agglutination of Con A to the *E. coli* in solution phase is the key reason for the signal amplification. Finally, as shown in the FIG. 9 insertion, when the incident angle of SPR was fixed at 54.32°, and the mixture of *E. coli* W1485 and Con A were injected into the Con A pretreated the mannose SAM chamber in which the concentration of Con A was fixed to be the same as that in curve C, the reflected light intensity change vs. time shows real time binding events. After about 70 min, the chamber was rinsed with PBS and SPR spectrum shows a significant angle shift 0.48° (Curve E). In summary, the amplification of binding between the mannose recognition element on the surface and *E. coli* W1485 by lectin Con A was observed by the SPR biosensor using a similar surface chemistry approach as in the QCM experiments.

Figure 10:
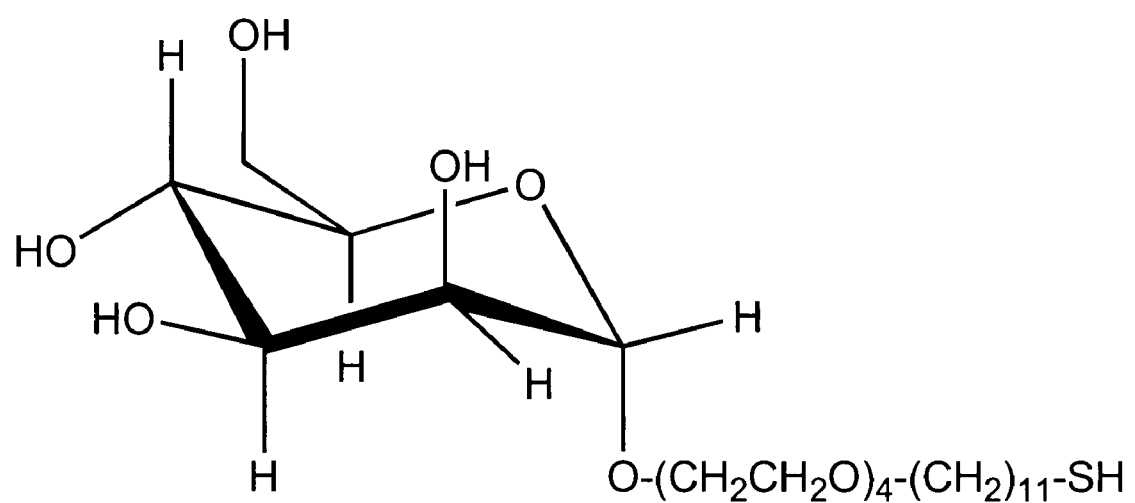
FIG. 10 is the molecular formula of a synthesized lipid mannose-SH used as a capture reagent for a surface plasmon resonance (SPR) QCM and Electrochemical Impedance Spectroscopy (EIS) biosensors.
Figure 11:
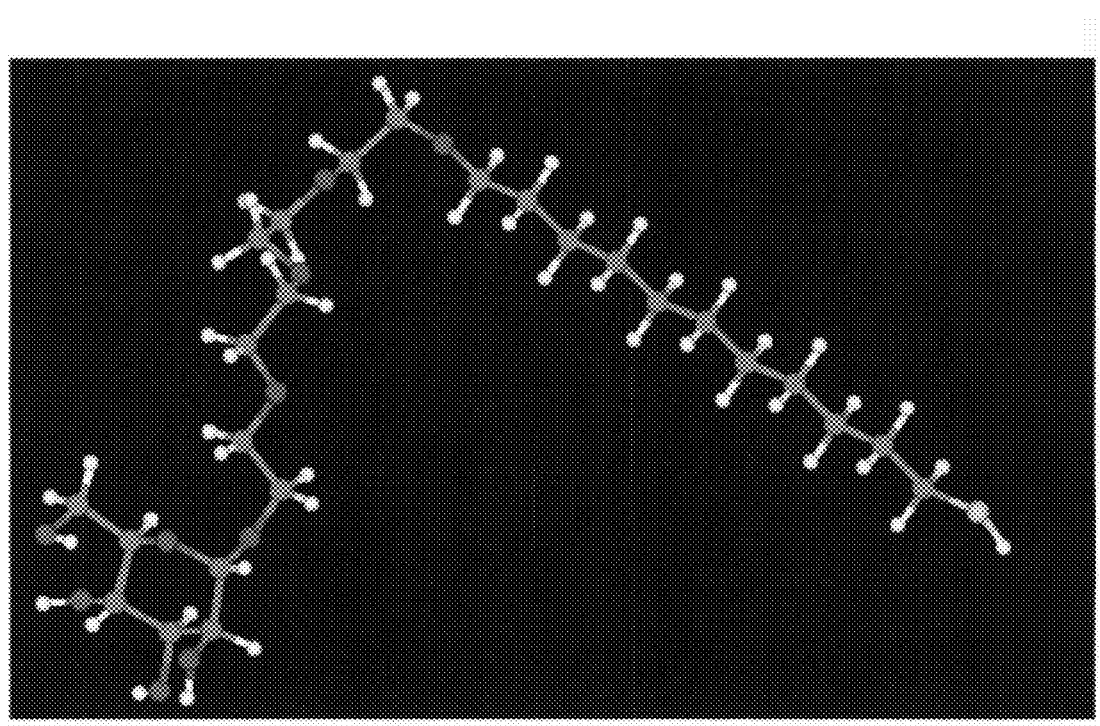
FIG. 11 is a three-dimensional model of the synthesized mannose-SH molecule used as the capture reagent for a surface plasmon resonance (SPR) biosensor. Black is oxygen and white is CH.
Figure 12A:
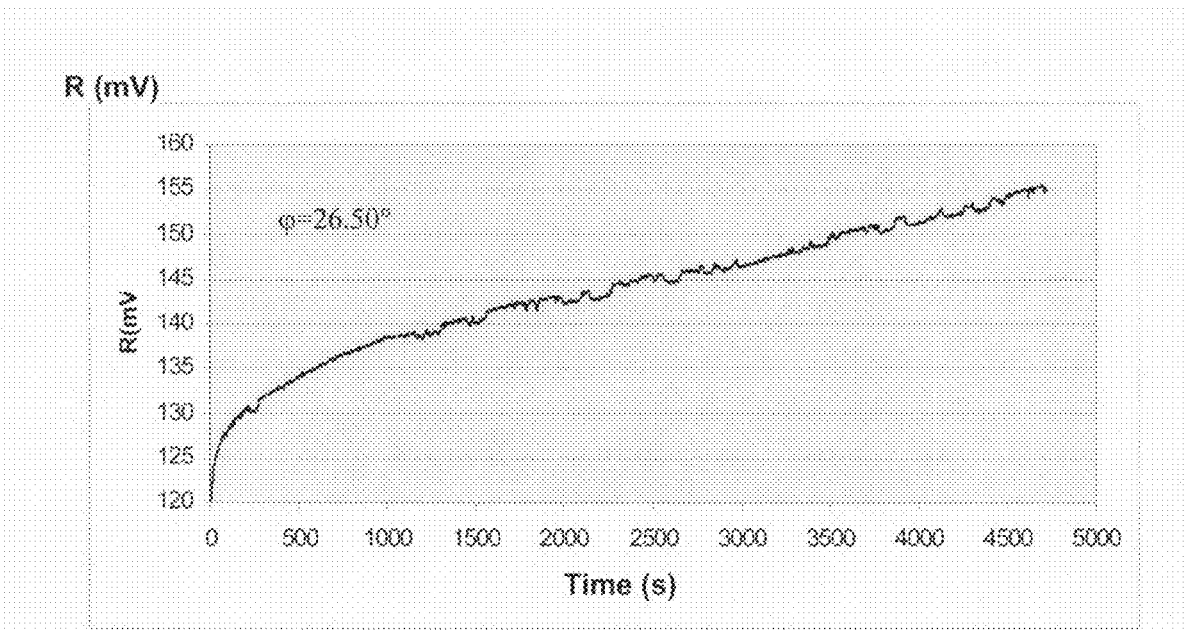
FIG. 12A is a graph illustrating mannose-SH binding to a gold surface of a surface plasmon resonance biosensor while the liquid in the chamber is ethanol. During measurements, the incident angle ϕ was fixed at 26.5°.
Figure 12B:
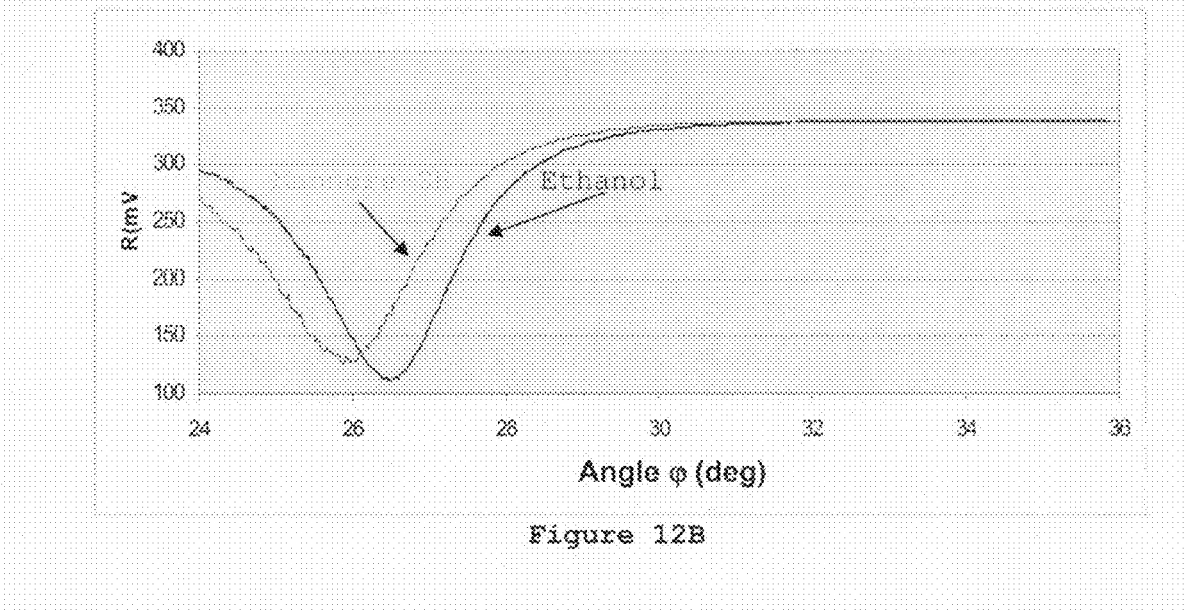
FIG. 12B is a graph showed the SPR spectra shift caused by Mannose-SH lipid in ethanol.
Figure 13A:
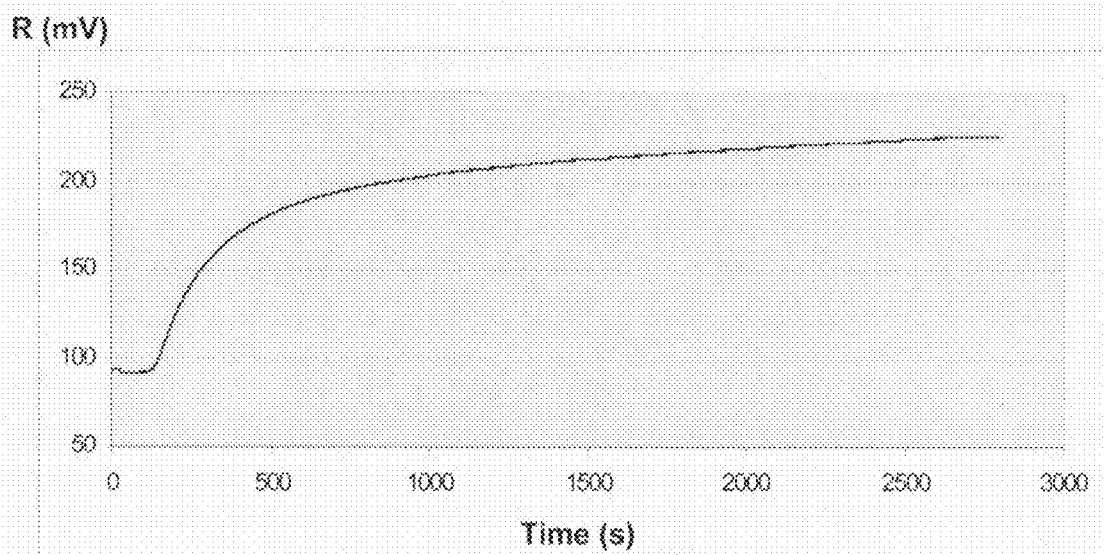
FIG. 13A and FIG. 13B are graphs illustrating protein Concanavalin A (Con A) in PBS buffer binding to the mannose-SH immobilized on the gold surface of the surface plasmon resonance biosensor. During measurements for FIG. 13A, the incident angle ϕ was fixed at 29.0°.
Figure 13B:
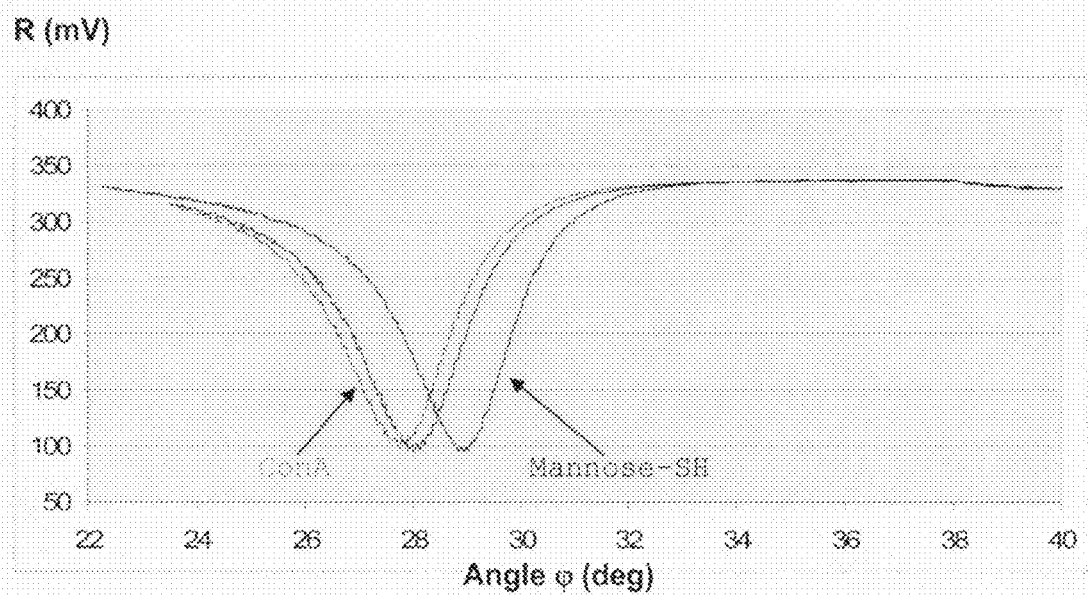
Figure 14A:
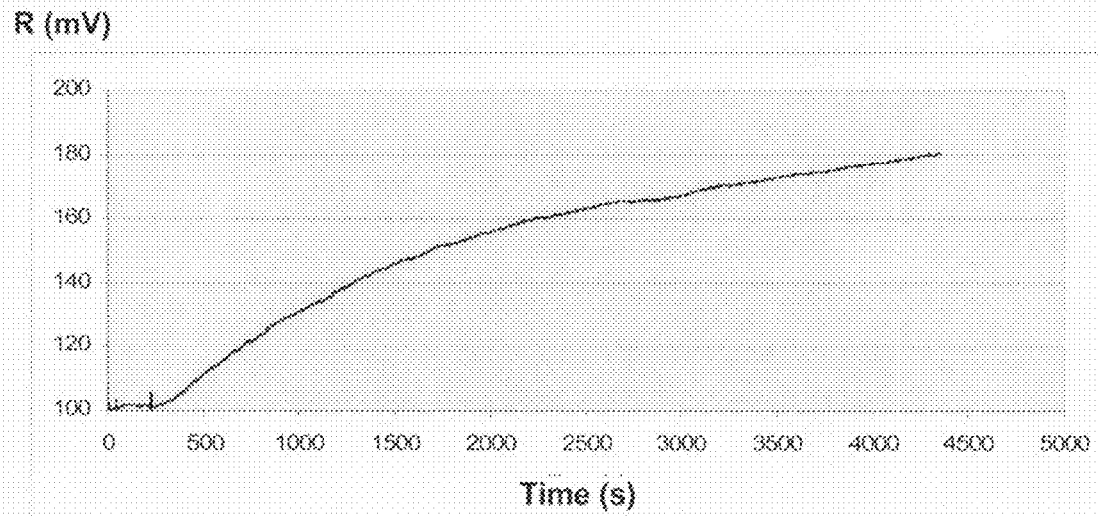
FIG. 14A and FIG. 14B are graphs illustrating *E. coli* w1485 binding to the Con A surface (immobilized on the mannose-SH lipid monolayer on the gold surface of the surface plasmon resonance biosensor if there are ConA molecules in the liquid. During measurements for FIG. 14A, the incident angle ϕ was fixed at 28.0°.
Figure 14B:
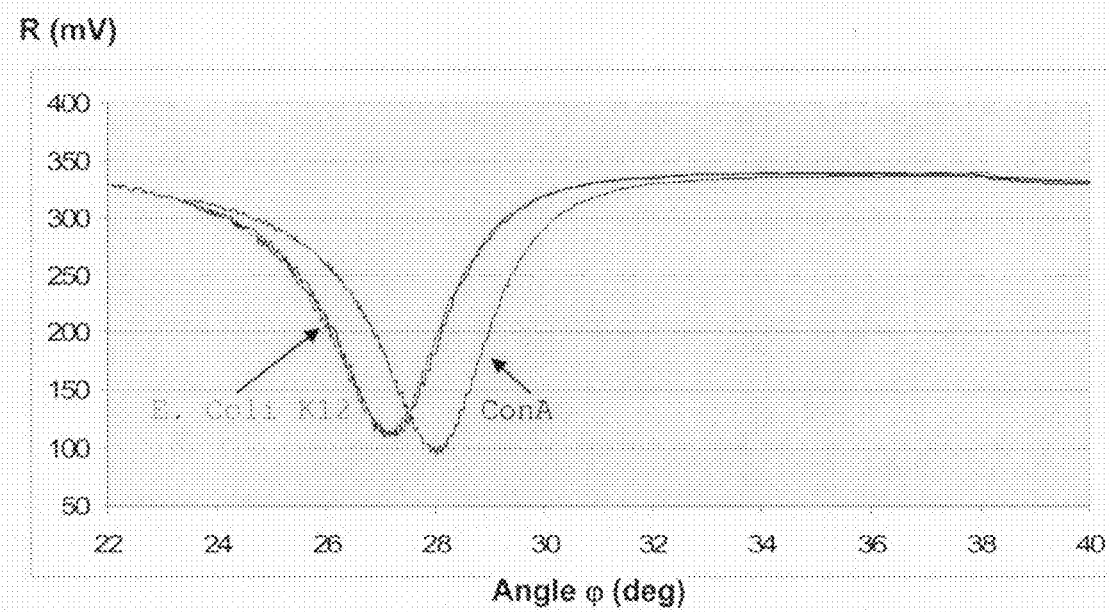

This example illustrates the use of a mannose-SH and ConA system with an SPR biosensor device. A portable SPR biosensor device as described in U.S. patent application Ser. No. 11/581,260 to Xiao and Zeng, filed Oct. 10, 2006, incorporated herein by reference in its entirety, was used to detect *E. coli* K12 with a bound lipid mannose-SH sample layer on the gold metallic film of the device. FIG. 10 illustrates the molecular formula of the mannose-SH as a capture reagent bound to gold (Au) thin metallic film 60 of the surface plasmon resonance biosensor device 10 described above. The mannose-SH molecule has a formula of $C_{25}H_{50}O_{10}S$ and a molecular weight (Mr.) of 542.31. A three-dimensional model of the mannose-SH is illustrated in FIG. 11. FIGS. 12A and 12B illustrate mannose-SH binding to the gold (Au) surface as the thin metallic film 60 of the surface plasmon resonance biosensor device 10, in ethanol. As illustrated in FIGS. 13A and 13B, the lectin concanavalin A (ConA) binds to the mannose-SH bound to the gold (Au) surface. *E. Coli* K12 can bind to the ConA surface if there is ConA in the liquid, as illustrated in FIGS. 14A and 14B.

Conclusion: Routine identification and characterization of toxins and micro-organisms are commonly performed by biosensors containing either antibodies or nucleic acid probes as the detection element. However, neither antibodies nor nucleic acids are necessarily the best or even most valuable means of identification. In order to have a realistic chance of detecting and identifying an unknown agent, a vast array of antibodies would be required. For DNA or RNA biosensors, often the DNA/RNA probe must be known and amplification of the DNA/RNA probe is needed before immobilization. Taking advantage of the fact that a high percentage of micro-organisms have both carbohydrates and carbohydrate binding pockets at their surfaces, we demonstrate here that a carbohydrate epitope in combination with a lectin amplification strategy is a real possibility for developing a highly sensitive and specific non-labeled biosensor for bacteria detection. The mannose QCM biosensor showed a significant improvement of the sensitivity and specificity for *E. coli* W1485 detection with a detection limit of a few hundred bacterial cells and a linear range from $7.5 \times 10^2$ to $7.5 \times 10^7$ cells/ml that is four decades wider than the mannose alone sensor. The change of damping resistances for *E. coli* adhesion experiments were no more than 1.4% suggesting that the bacterial attachment was rigid, rather than a viscoelastic behavior. Little non-specific binding was observed for *Staphylococcus aureus* and other proteins (Fetal Bovine serum, *Erythrina cristagalli*). Carbohydrate epitopes offer several advantages over antibody/nucleic acid detection of antigens. Carbohydrates possess broad interaction specificity; carbohydrate recognition could enable identification of unexpected or even novel agents. Carbohydrates do not denature or lose activity upon changes of temperature or pH; they are stable and could have long lifetime. Oligosaccharides are smaller than antibodies; consequently, higher densities of carbohydrate sensing elements could lead to higher sensitivity and less non specific adsorption. A few carefully chosen carbohydrate epitopes in combination with additional specificity of lectin-bacteria recognition could provide the desired fingerprinting of a high number of biological agents and have a propensity to be extremely specific for one particular biological agent, possessing minimal cross-reactivity for other agents. In addition, combining lectin and carbohydrate SAM recognition allows rigid binding of bacteria to the QCM sensor surface, which significantly enhances specificity and sensitivity of detection. The present invention provides sensor devices highly suitable for the fast, reversible and straightforward on-line detection of these analytes at very low concentrations in complex samples.

The present invention also provides a two dimensional carbohydrate-lectin-array that allows for multitude of discrete carbohydrate protein interactions of bacterial cells to be observed simultaneously, thus resulting in a high throughput probe of cell surface carbohydrate and lectin adhesin expression using a non-labeled sensor readout. The array technology is easy to assemble since only the carbohydrate is immobilized on the transducer surface which avoids the loss of binding activity of lectin due to immobilization. The measurement is rapid, sensitive, specific, convenient and label free which allows real time monitoring of the dynamic changes of cell surface carbohydrate and lectin adhesin expression as well as the detection of bacteria with extremely high sensitivity and specificity. The label free microarray format enables the real time measurement of complicated carbohydrate-protein interactions with thousands of unique glycans and lectins while consuming only very small amount of precious reagents. The high density of the immobilized carbohydrate on the array surface not only enhances the binding sensitivity but also accommodates the multivalent binding. The miniaturized and high throughput nature of microarrays makes them a tool to profile cell surface carbohydrate and lectin adhesin expressions and to deliver high quality, high information content. Since carbohydrate and/or lectin adhesin-cell interactions are ubiquitous in nature, this improvement has the potential to impact a variety of important areas.

Thus, functionalized self-assembled monolayers (SAM) of specific carbohydrates on gold surface using thiol SAM and click chemistry are provided. Selected monosaccharides and a preferred polysaccharides are modified to facilitate their coupling to gold transducer surface for carbohydrate array fabrication.

Figure 15:
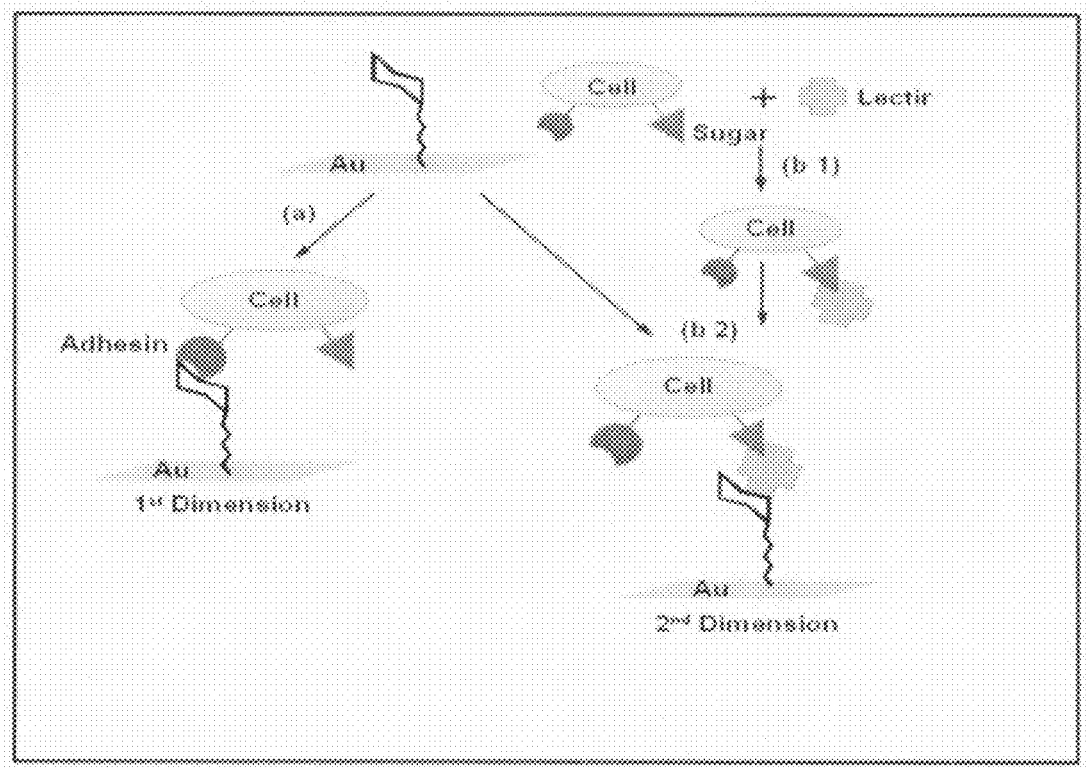
FIG. 15 is a schematic diagram of 1 and 2 dimensional carbohydrate-lectin microarrays.

FIG. 15 shows a schematic diagram of the basic 2-dimensional carbohydrate lectin microarray of the present invention described previously. The carbohydrate SAMs developed are used in combination with various available lectins for a carbohydrate-lectin microarray. Profiling and detection of eight pathogenic category B bacteria (Diarrheagenic *E. coli*, Pathogenic *Vibrios* and *Salmonella*) and two non-pathogenic bacteria controls via two compatible orthogonal label free transduction mechanisms (i.e. electrochemical Impedance spectroscopy (EIS) and quartz crystal microbalance (QCM)) is described. The sensitivity, selectivity, dynamic range and limit of detection and the binding pattern of the carbohydrate-lectin arrays are evaluated and validated using these 10 bacterial strains.

Using standard fabrication processes, the carbohydrate-lectin array platform is integrated with microfabricated electrodes to incorporate electrochemical impedance and quartz crystal microbalance readout for high throughput, simultaneously profiling of bacterial cell surface carbohydrate and lectin adhesin expression. A 5×5 2D carbohydrate-lectin array is fabricated and tested to obtain the expression pattern of the selected 10 bacteria targets. Subsequently, a larger array that incorporates oligosaccharides and anti-carbohydrate antibodies can be used.

The biosynthesis and expression of any particular cell membrane constituent is a function of age and the physiological state of the cell as well as the cellular growth environment. Recently there has been increasing evidence that glycosylation plays an important role in diverse biological processes such as cell signaling, cell adhesion[5,6], fertilization[7,8], proliferation[9], viral/bacteria infection, apoptosis and the immune response[10] as well as for many disease states. However, during the study of cell-cell interactions, the proximity of other cell surface constituents can interfere with the ability of receptors to bind the ligand. Thus, when comparing the binding of a given ligand to cells under varying physiological conditions, it is often not possible to determine whether any difference observed is due to a change in the numbers of receptor molecules, alternations in the recognition-site, or interference by other surface constituents. As a consequence, unraveling the secrets of glycosylation has become a key research focus in glycoscience and served as a fundamental requirement for both basic and translational research. Efforts toward this end have catalyzed the formation of a Consortium for Functional Glycomics (http://gycomics.scripps.edu), which aims to "understand the role of carbohydrate-protein interactions at the cell surface in cell-cell communication". The identification of a proper carbohydrate scaffold has become the prerequisite to the characterization of carbohydrate-protein interactions. Over the past ten years, a plethora of sugar scaffolds have been explored for studying the carbohydrate-protein interactions[11]. At the same time, the field has seen growing interest in the development of glycoarray technology, i.e. displaying carbohydrates on surface, which aims at mapping the carbohydrate-protein interaction in a high throughput manner. Methods were developed to immobilize a variety of oligosaccharides, glycolipids, or glycoproteins to the solid supports to probe the carbohydrate binding properties of proteins or cells. Although these glycoarrays provide valuable information about carbohydrate-protein interaction. The main disadvantage of most of the current glycoarrays is that little is learned about the nature of the interactions and information about changes in glycosylation is difficult to obtain.

A panel of specific monoclonal antibodies, each of which could recognize a unique structure and could be used to readily identify and isolate specific oligosaccharides within a complex mixture. However, it is well known that carbohydrates are poorly immunogenic and production of high affinity carbohydrate binding antibodies using traditional approaches is expensive and time consuming. Fortunately, nature has already provided a vast number of carbohydrate-binding proteins called lectins. Lectins are produced by all living things. Many of these lectins are known to be important for promoting cellular adhesion and acting as receptors for other glycoconjugates. Most lectins have high affinity interactions with specific carbohydrate determinants, and thus lectins can be used to characterize and isolate glycoconjugates on the basis of specific structural features, instead of the size or charge of the glycans. In addition, lectins can be used in a manner akin to antibodies, in matrices, or on intact glycoproteins, and to study the biosynthesis of glycoconjugates.

Many Lectins interact with bacteria by binding to the myriad of carbohydrate structures present on the cell surface, e.g. techoic acids, lipopolysaccharides, and peptidoglycans. Lectins are generally specific for a particular carbohydrate structural motif. Many bacterial species may bind to a single lectin and a single species may bind a variety of lectins with different carbohydrate specificities. This latter characteristic has been used to develop lectin arrays to analysis of bacterial cell surface glycosylation. Dynamic alternations of the carbohydrate components and distinguish glycopatterns of four *E. coli* bacteria were obtained using a lectin microarray. However, there are several limitations for lectin arrays. First, only accessible carbohydrate motifs rather than the entire glycome are visualized due to limited availability of lectins.

Second, there is an inherent poor coating efficiency of lectin proteins as well as an altered availability of their epitopes due to the surface immobilization-associated features. Third, carbohydrate-lectin interactions are often weaker than antibody-antigen interactions, by perhaps a factor of $10^2$-$10^3$ from typical antibody equilibrium dissociation constant ($K_D$). Finally, the reliance on traditional detection systems such as fluorescence can be a serious drawback since false positive results could be produced due to high background fluorescence. There is an increasing need for new tools that permit fast and systematic investigations of the complex glycobiology inherent in cellular systems for well defined scientific studies.

The interaction of lectin to carbohydrate, is not a simple monomeric binding event, but an oligo- or polymeric binding mechanism.[12] Lectins often have more than one carbohydrate binding site, and it has been shown that the occurrence of two simultaneous binding events can increase the avidity of interaction by more than 100-fold,[12] and even as high as $10^4$-fold. The present invention takes advantage of the polyvalent binding situation of lectin to carbohydrate by integration of the two lectin-carbohydrate binding events (i.e. use the same lectin as a bridge to link cell surface glycosylation site to the carbohydrate immobilized on the sensor surface). The previous examples show that the lectin mediator increases the contact area between cell and carbohydrate on the sensor surface and leads to rigid and strong attachment of bacterial cells to the carbohydrate immobilized on the QCM transducer. By using lectin Con A as a mediator, over $10^4$ fold increase in binding sensitivity for binding with an *E. coli* was observed for a mannose sensor than that of without using Con A mediator, thus significantly increase the sensitivity and specificity of bacterial detection.

Bacterial cell surfaces often express both carbohydrate and lectin adhesin structures. Thus, it is highly feasible to apply a carbohydrate sensor in a two dimensional manner to patterning both cell surface expressed carbohydrates and lectin adhesins. In the first dimension, the carbohydrate sensor directly senses the bacterial cell surface lectin adhesins, in the second dimension, the carbohydrate sensor senses the bacterial cell surface carbohydrate structures using lectin mediators. Therefore, the carbohydrate-lectin array involves three binding events: two carbohydrate-lectin recognitions and one lectin adhesin-carbohydrate recognition and allows high information content of bacterial cell surface carbohydrate and lectin expression profiling with surface sensitive QCM, SPR, or EIS transducer. The 2 dimensional carbohydrate-lectin microarray for profiling bacterial cell surface carbohydrates and lectin adhesins is used for detection and specific identification of bacterial pathogens.

Figure 16:
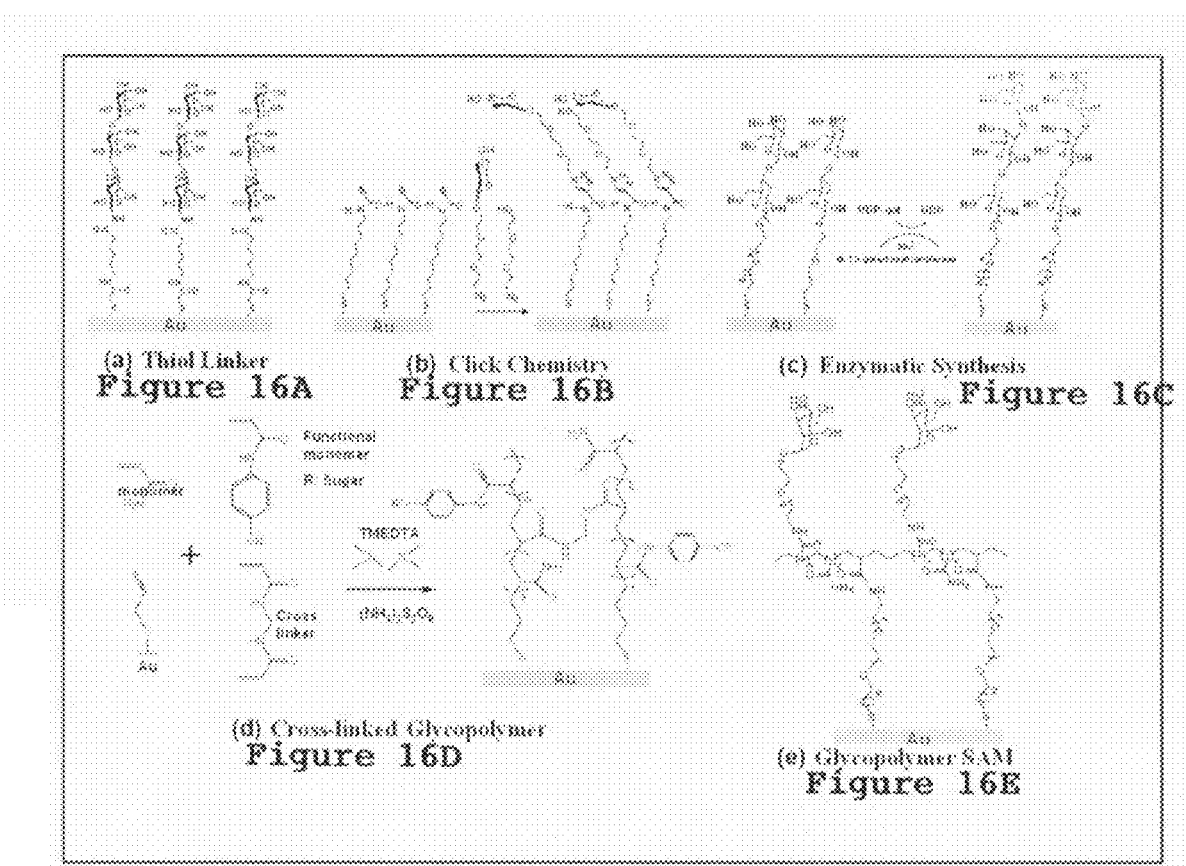
FIG. 16 is a schematic representation of various Carbohydrate SAM and glycopolymer fabrications: A) *Studying the interaction of alpha-Gal carbohydrate antigen and proteins by Quartz-Crystal Microbalance (QCM) JACS*, 2003, 125, 9292; B) *Studying of Carbohydrate-Protein Interactions by "Clicked" Carbohydrate Self-Assembled Monolayers Anal. Chem.* 2006; 78; 2001; C) *Enzymatic Synthesis of Oligosaccharides on Carbohydrate Self-Assembled Monolayers, in preparation*; D) *Cross-linked Surface-Grafted Glycopolymer for Multivalent Recognition of Lectin, Anal. Chem. in review*; E) *Alkanethiol Containing Glycopolymers: A Tool for the Detection of Lectin Binding, Bioorganic & Medicinal Chemistry Letters, in revision*.

Three approaches have been successfully demonstrated to fabricate versatile carbohydrate SAMs with well-defined structures on the gold sensor surfaces. Shown in FIG. 16, in the first example, α-Gal trisaccharide was tailored with a thiol linker, which facilitates the formation of SAMs on the gold surface (FIG. 16A). The binding between α-Gal trisaccharide and anti-Gal antibody was thoroughly studied. In the second example, the use of surface clicking reaction was explored, specifically the Cu(I)-catalyzed Huisgen 1, 3-dipolar cycloaddition reaction, for anchoring sugars onto preformed SAM. This fabrication was based on pre-formed SAM templates incorporated with alkyne terminal groups, which could further anchor the azido-sugars to form well-packed, stable and rigid sugar SAMs (FIG. 16B).

In the third example, enzymatic glycosylations and in-vitro enzymatic synthesis of polysaccharides on a pre-sugar SAM (FIG. 16C) was examined. In order to study the multivalent effects of carbohydrate-lectin interactions, alkanethiol containing glycopolymers (FIG. 16E) and cross-linked surface-grafted glycopolymer (FIG. 16D) were developed. These experiments provided efficient fabrication methods of various carbohydrate scaffolds on the gold surface and provide a versatile analytical tool to investigate the carbohydrate-protein interaction and the biosynthetic pathways of polysaccharides. It was also demonstrated that the carbohydrate SAMs in concert with non-labeled transducers (i.e. QCM, SPR and EIS)) offered a promising tool for high-throughput characterization of carbohydrate-protein interactions. Such a combination should complement other methods such as ITC and ELISA and provide insightful knowledge of the corresponding complex glycobiological processes.[13]

Figure 17:
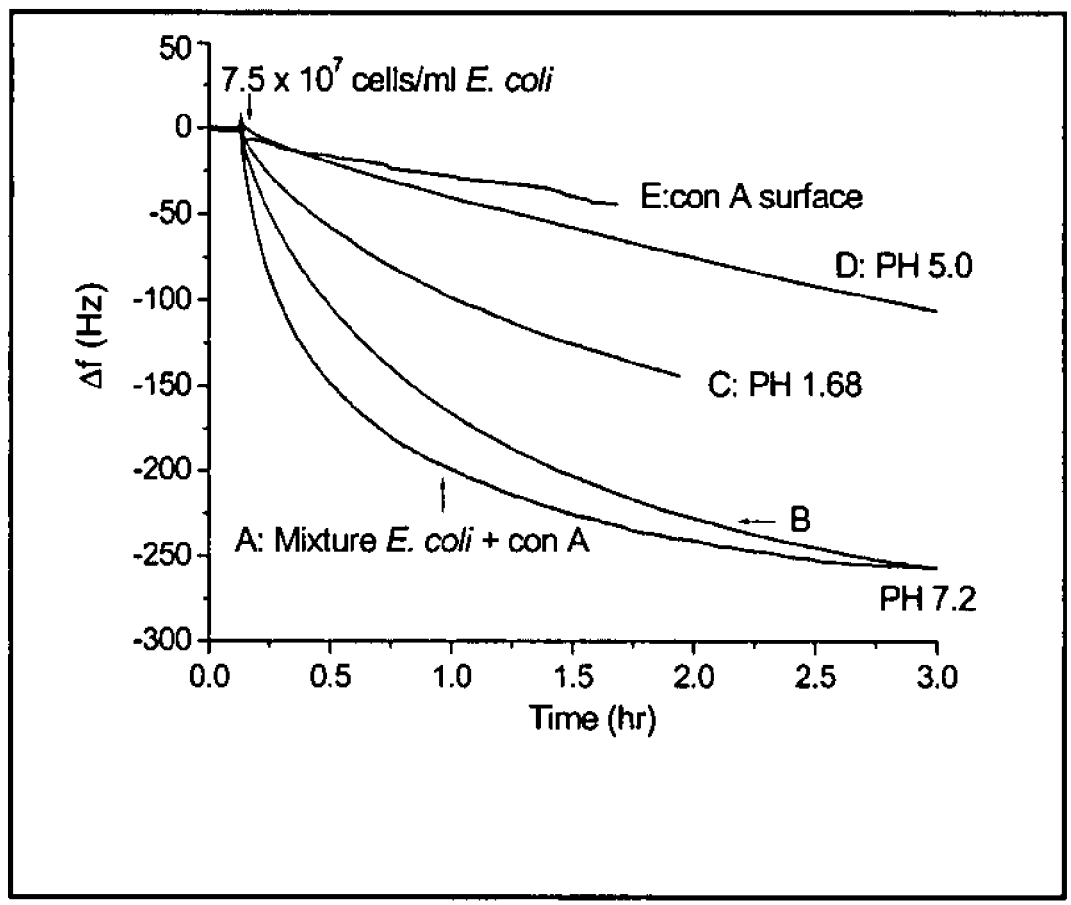
FIG. 17 QCM real time ΔF vs. time curve; (A) Adding *E. coli*/Con A mixture to mannose sensor (pH. 7.2); (B-D) Adding *E. coli* to con A treated mannose sensor at different pH; (E) Control: Adding *E. coli* to con A-modified surface.

Experimental conditions were studied to unquestionably demonstrate that the Con A adsorbed on the E. coli cell surface facilitates the binding of E. coli to the mannose receptor rather than free Con A in the mixture of bacteria that binds to the mannose receptor. Two conditions were studied. In one, a low concentration of Con A was first added to the mannose sensor test chamber. The concentration of Con A added is relatively low so that the mannose surface is not saturated based on the Con A/mannose binding study and the surface still has a plethora of available mannose binding sites (FIG. 17 Curves B, C, D); In another, the same concentration of Con A was spiked directly to the bacterial cells (Curve A) and then applied to the carbohydrate sensor surface. FIG. 17 Curves A and B show that there is no difference of the equilibrium amount between adding Con A first on the sensor surface or on the bacterial cell sample. This result is highly significant and allows simple development of carbohydrate-lectin array. Lectin can be spiked into the cell sample, and then added to the array or we can add lectin first to the carbohydrate array then add bacterial sample.

Con A has an isoelectric point of about pH 5 and requires calcium or manganese ions at each of its four saccharide binding sites. At neutral and alkaline pH, Con A exists as a tetramer of four identical subunits of approximately 26,000 daltons each. Below pH 5.6, Con A dissociates into active dimmers of 52,000 daltons. The study was how ConA multivalency situation affects its role as a mediator. FIG. 17, curves B (pH 7.2), C(pH1.68) and D(pH5.0) show that at physiological pH 7, while Con A is a tetramer, gives the highest binding sensitivity. Thus, the higher multivalency of the lectin, the higher efficiency of conjugation of the lectin to both the cell surface carbohydrate and carbohydrate sensing element.

Figure 18:
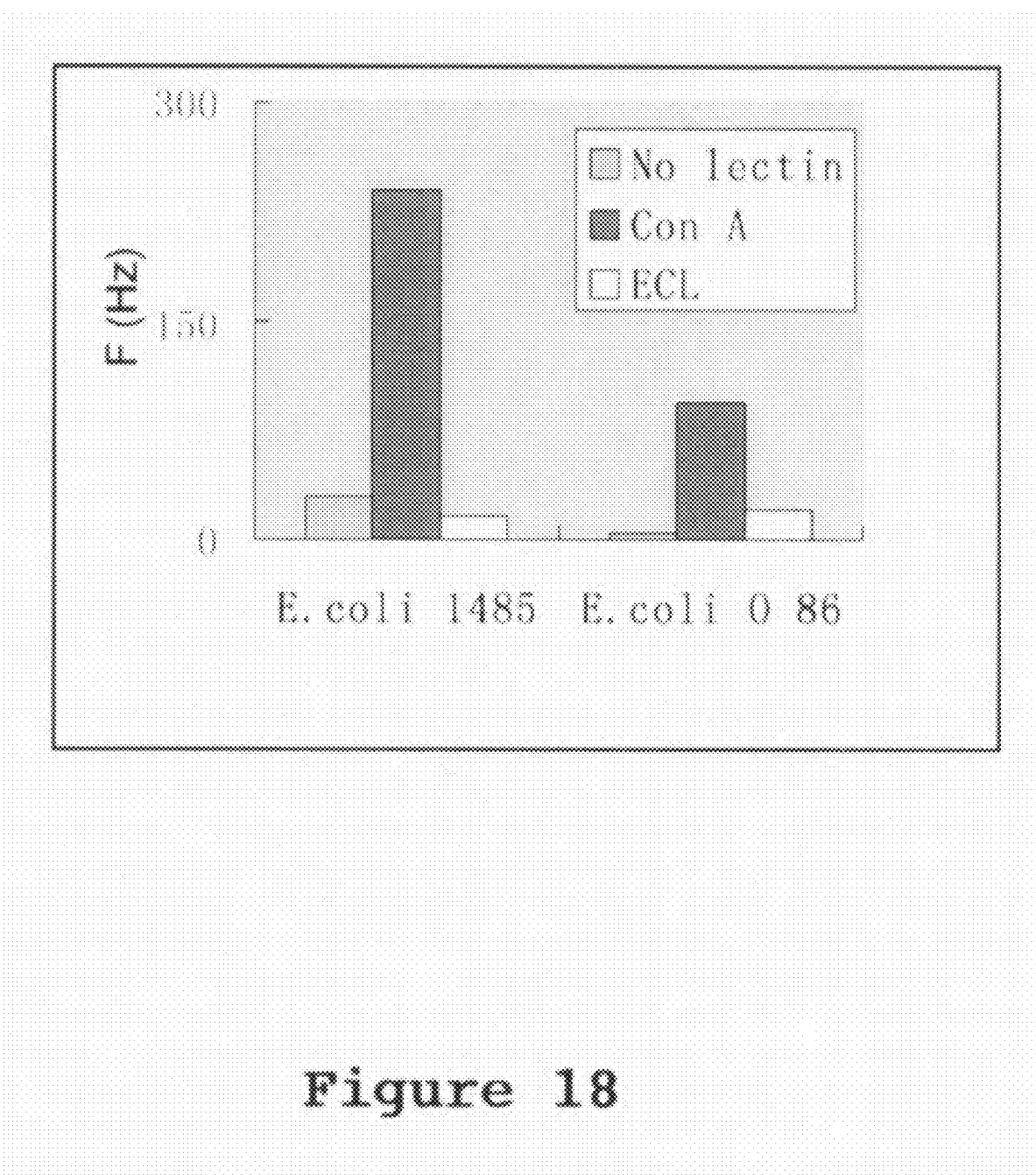
FIG. 18 Binding pattern of *E. coli* 1485 and 086 on mannose-sensor using ConA or ECL lectin mediator.

Two lectins (Con A and ECL) were used with a mannose sensor to obtain the carbohydrate and lectin expression pattern of E. coli 1485 and 086. As shown in FIG. 18, the binding patterns of E. coli 1485 and 086 were distinguished on the mannose carbohydrate sensor. This verified the feasibility of the proposed approach.

Figure 19:
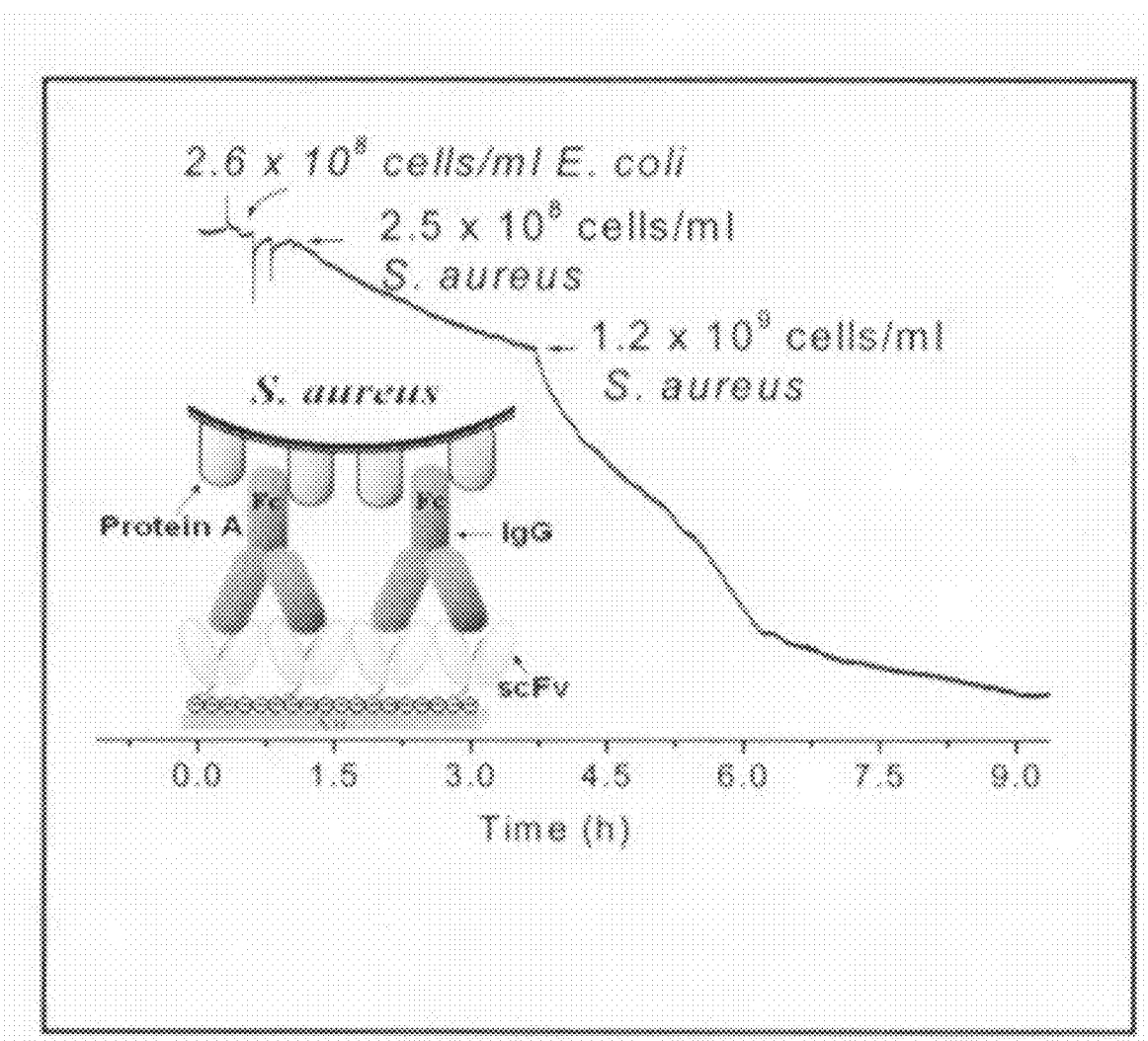
FIG. 19 scFv biointerface for *S aureus* detection. QCM real time ΔF vs. time curve.

The multivalency of an antibody was explored to mediate the recognition of bacterial cell surface proteins. Shown in FIG. 19, a recombinant antibody was immobilized on the gold surface and it binds with rabbit IgG. Using rabbit IgG, it allows multivalent antibody mediated recognition of S. aureus surface protein A. Protein A is a cell surface component of S. aureus. All but 1 of 143 strains of S. aureus were positive for protein A, whereas all 34 strains of Staphylococcus hyicus and 123 of 127 strains of Staphylococcus intermedius were devoid of this cell wall component.[20] The presence of protein A on the cell wall is an accepted criterion for the identification of S. aureus. Protein A is a well known Fc receptor which binds to the γ heavy chains, the Fc portion of the immunoglobulin. The sandwich antibody assay allows the specific orientation of Fc capture agents by immobilization through recombinant antibody scFv and consistently increases the analyte-binding capacity of the surfaces, with up to 7-fold improvements over surfaces with randomly oriented IgG capture agents (data not shown). Non-specific binding of E. coli to the scFv sensor is very small (the S. aureus sample was pretreated by 0.1 M Na-citric acid elution buffer (pH 2.8) to remove the IgG bond on the surface). Thus, the proposed carbohydrate microarray can be easily expanded by incorporating antibodies for lectins or carbohydrates to profile the whole glycome that can overcome the problems of limited availability of lectins.

The technology needed for a carbohydrate-lectin array is provided that allows rapid profiling cell surface carbohydrate and lectin expression for bacterial detection. It also provides valuable tool for cell analysis. For example, antibiotic-induced release of lipopolysaccharides (LPS) also called endotoxin was reported to be an important cause of the development of septic shock in patients treated with severe infections caused by gram-negative bacteria. (ref: van Langevelde, P.; Kwappenberg, K. M. C.; Groeneveld, P. H. P.; Mattie, H.; van Dissel, J. T. "Antibiotic-induced lipopolysaccharide (LPS) release from *Salmonella typhi*: Delay between killing by ceftazidime and imipenem and release of LPS." *Antimicrobial Agents and Chemotherapy* 1998, 42, 739-743.: Tamaki, S.; Sato, T.; Matsuhas. M "Role of Lipopolysaccharides in Antibiotic Resistance and Bacteriophage Adsorption of *Escherichia-Coli* K-12." *Journal of Bacteriology* 1971, 105, 968-). The array can therefore elucidate the role of antibiotics on the dynamics of bacterial carbohydrate and lectin expression by an investigation of real time changes in the carbohydrate and lectin expression patterns. It will provide a measure of endotoxin release so important to septic shock complications in infectious diseases as well as provide essential information towards synergistic use of endotoxins binding and neutralizing agents in conjunction with antibiotics.

There are two key technologies: carbohydrate SAM fabrication and carbohydrate-lectin microarray development. The results presented above show the glycosurface chemistry, the characterization of the carbohydrate-protein interaction, the lectin-carbohydrate label free microarray platform technology.

are not yet completely understood and may vary according to the molecular structures of the groups presented at the surfaces. Therefore, a general "bi-functional" linker as shown is used. This linker consists of polyethylene glycol ($[OCH_2CH_2]_nOH$, n=3-6) portion and saturated alkyl portion ($R=(CH_2)_{11-14}$). For the alkanethiolate sugar SAM, the polyethylene glycol port is linked with carbohydrate ligands, while the alkyl portion is terminated with —SH group which will anchor the molecule on the Au surface of QCM sensor. For click chemistry sugar SAM formation, a bifunctional

TABLE 2

Pathogenic bacterial targets and carbohydrate and lectin array components.

| Bacterial isolates | O-antigen structure | Biosynthetic gene cluster (Accession #) | Binding lectin |
|---|---|---|---|
| E. coli O8/9 | →3)-β-D-Man-(1→2)α-D-Man-(1→2)-α-D-Man-(1→ | AB010150 | α-Man: Canavalia ensiformis (Con A) |
| E. coli O26 | →3)-a-L-Rha-(1→4)-a-L-FucNAc-(1→3)-b-D-GlcNAc-(1→ | DQ196413 | GlcNAc: Datura stramonium (DSA) |
| E. coli O128 | →6)-b-D-Gal-(1→3)-b-D-GalNAc-(1→4)-a-D-Gal-(1→3)-b-D-GalNAc-(1→ | AY217096 | GalNAc: Helix pomatia (HPA) |
| E. coli O157 | →2)-a-D-Per4NAc-(1→3)-a-L-Fuc-(1→4)-b-D-Glc-(1→3)-a-D-GalNAc-(1→ | AF061251 | α-Fuc: Anguilla anguilla (AAA) GalNAc: Helix pomatia (HPA) |
| S. enterica O35 | α-Col-(1→6) \| →4)-α-D-Glc-(1→4)-α-D-Gal-(1→3)-β-D-GlcNAc-(1→ \| α-Col-(1→3) | AF285969 | GlcNAc: Datura stramonium (DSA) α-Glc: Canavalia ensiformis (Con A) |
| S. enterica B | α-D-Abe-(1→3) \| →2)-α-D-Man-(1→4)-α-L-Rha-(1→3)-α-D-Gal-(1→ | X60756 | α-Man: Canavalia ensiformis (Con A) |
| S. enterica E1 | →6)-β-D-Man-(1→4)-α-L-Rha-(1→3)-α-D-Gal-(1→ | X60665 | α-Man: Canavalia ensiformis (Con A) |
| V. cholerae O139 | α-Col-(1→2)-β-D-Gal-(1→3) \| →6)-β-D-GlcNAc-(1→4)-α-D-GalA-(1→3)-β-D-QuiNAc-i \| α-Col-(1→4) | Y07786 | GlcNAc: Datura stramonium (DSA) |

Bacterial surface lectin adhesin and carbohydrate structure play important role in adhesion and infection. Therefore, they are the ideal model system to verify the principle. Table 2 lists the carbohydrates and lectins that can be used to assemble the 2 D array as well as 8 pathogenic bacterial targets. Two nonpathogenic strains are used (*E. coli* 086 and 1485) as controls. Several bacterial strains and types are selected that have same lectin binding activity to evaluate and verify the potential high specificity of the two dimensional carbohydrate-lectin array. The difference of lectin adhesin expression pattern can allow high specific identification of those bacteria with similar lectin binding specificity. The glycosylation and lectin adhesin pattern obtained can be used for rapid, point of care detection of bacteria. Five by five (5×5) arrays using 5 carbohydrates and 4 lectins to profile 10 bacteria in Table 1 are provided. The assay will make a significant impact in the glycoscience and in the areas of infectious diseases and screening and determination of harmful pathogens for clinical diagnosis and environmental monitoring.

Figure 20:
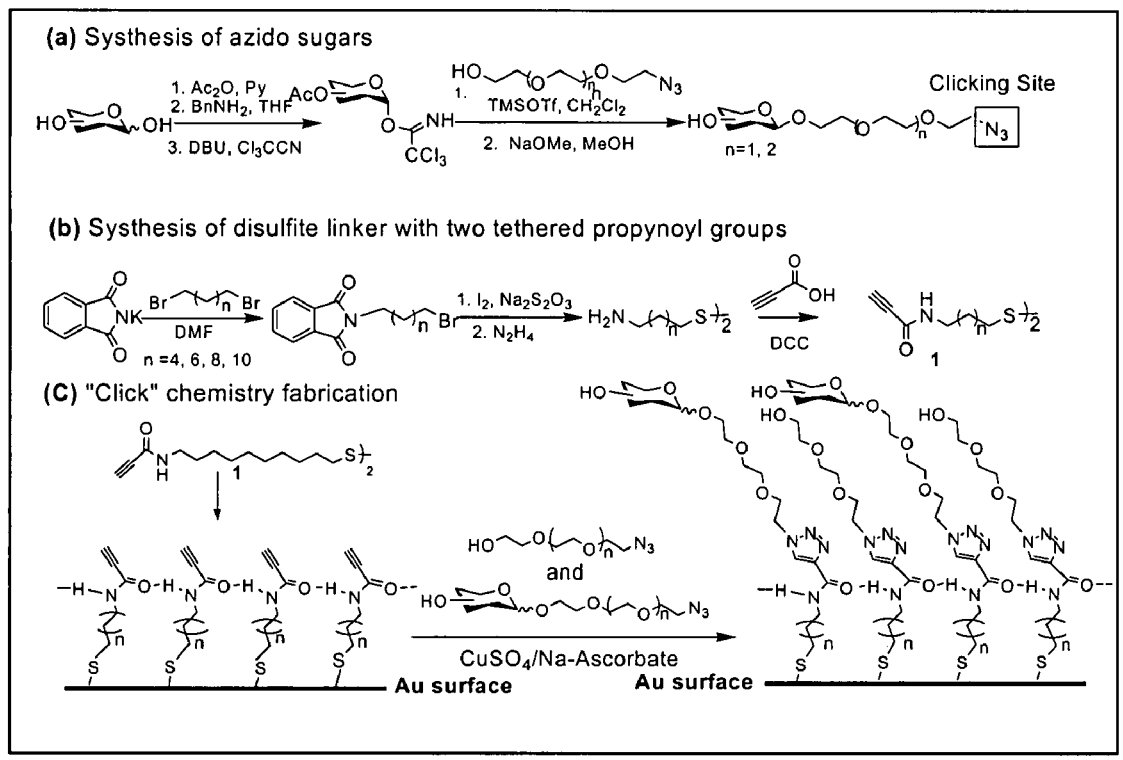
FIG. 20 is a schematic diagram of a "Click" chemistry fabrication strategy.

Monolayers of terminated in short oligomers of the ethylene glycol group ($[OCH_2CH_2]_nOH$, n=3-6) prevent the adsorption of virtually all proteins under a wide range of conditions. The mechanisms responsible for such resistance linker consisting of a saturated alkyl portion with a thiol group and a clicking site at each end are made (FIG. 20). A disulfite linker with varied chain length with two tethered propynoyl groups can be synthesized. This common immobilization strategy offers an array of "clicking" functionalized SAMs ready for fabrication with different clicking sugars. In terms of SAM formation, the disulfites are undistinguished from the free thiol groups, while the former are more stable and easy to handle (FIG. 20C). Another advantage comes from the amide linkage connecting the propynoyl group and the alkyl chain. A number of previous reports have shown that the internal amide groups tend to form lateral hydrogen-bonding network that improve the stability of the SAM.

In a sugar library, all of the sugar precursors share a common design motif ethylene-glycol (OEG) with a pendant oligo-tethered either with HS or azido groups as shown in FIG. 20. Detail below is the two methods for sugar precursor synthesis.

Synthesis of Sugar Alkanethiolates

The synthesis of sugar-linker-SH is showed in FIG. 20 The linker (1) is connected to sugar via a glycosylation reaction promoted by $HgBr_2$ and $Hg(CN)_2$.

"Click" Chemistry Fabrication Strategy:

Peracetylated Schimdt's sugar donors were coupled with azido-OEG-OH to afford the desired products. Several azido sugars were synthesized using this method with the coupling yields in the range of 60-80% (FIG. 20A). Azido sugars are clicked onto the preformed alkynyl groups terminated monolayer. The density of the sugar can be controlled by tuning the molar ratio of azido-oligoethylglycol ($N_3$—OEG-OH, the dilute linker) and azido sugar. To block any unoccupied click sites, the obtained monolayer are further treated with azido-oligoethylglycol linker under the clicking conditions. This click step helps to maintain a highly packed and rigid sugar monolayer.

Carbohydrate-Lectin 2D Array Fabrication and Characterization (Objective 2).

The carbohydrate-lectin 2D array fabrication involves development, evaluation and validation of three distinct phases: (1) covalent attachment of carbohydrates to microarray surfaces using above linking chemistry; (2) lectin tagging of the target bacterial cells; (3) specific binding of target bacterial cells as well as lectin tagged bacterial cells to the immobilized carbohydrates.

Carbohydrate Microarray Fabrication (1 Dimension)

The fabrication of carbohydrate SAM is the pivotal step for the formation of stable robust sensors. Each carbohydrate (i.e. Glucose (Glc), Mannose (Man), Fucose (Fuc), N-acetyl Glucosamine (GlcNAc) and N-acetyl Galactosamine (GalNAc)) on Table 3 is immobilized at optimal concentration with proper spacing to obtain the highest possible binding capacity for the binding protein. Consequently, the two coupling methods described above, the concentration of the clicking carbohydrate, types and concentration of diluent spacers and blocking reagents, gold surface roughness on the quality of the film are determined to provide the optimal combination for generation of carbohydrate immobilized layer. The Au quartz crystal is cleaned with 1:1 mixed concentrated acids ($HNO_3$: $H_2SO_4$) and dried gently with nitrogen. The dry frequency of the modified Au electrode will be measured at each step of immobilization to estimate the surface coverage.

Gold surface Roughness: The surface roughness can affect the order and rigidity of immobilized sugar SAM. Two Au surfaces (polished and non-polished) at two frequencies, 10 M Hz and 25 M Hz AT cut quartz crystal are used. The use of unpolished surfaces allows a measure of how surface roughness (i.e. crystallographic orientation of Au) affects the quality of immobilization of carbohydrate.

Ligands presenting density and spacing Fine tuning of ligand density is accomplished by changing the ratio of functionalized OEG-thiol and diluent OEG-thiol. The strategies are tested to obtain sugar with optimal spacing by using various length and concentration of dilutet OEG-thiol for the optimum binding with lectin and on effects of potential steric hindrance on the binding of lectin.

Surface resistance to nonspecific adsorption: The non-specific adsorption is assayed with three non-carbohydrate binding proteins, fibrinogen, lysozyme and BSA. Fibrinogen, a large (340 kD) blood plasma protein that adsorbs strongly to hydrophobic surfaces, is used as a model for "sticky" serum proteins and lysozyme, a small protein (14 kD, pI=12) that is positively charged under the conditions of the experiment (phosphate buffered saline, PBS, pH 7.2) is often used in model studies of electrostatic adsorption of proteins to surfaces. BSA has been traditionally used as blocking protein to occupy any uncovered sensor surface to eliminate non-specific adsorption. BSA allows evaluation of the overall non-specific adsorption of the sugar monolayers.

Choice of blocking reagents: After the carbohydrate is immobilized with suitable spacers inserted, if nonspecific adsorption still occurs, blocking agents are added, to further reduce nonspecific adsorption. The effects of various blocking reagents on the sensitivity and non-specific binding of protein with carbohydrate-SAM is determined. Super Block®, ovalbumin, fish gelatin and albumin are used at various concentrations and times.

Carbohydrate Microarray Characterization

Following each immobilization step as described, the obtained surface immobilized layer is characterized by multi-techniques (e.g. Cyclic Voltammetry, Electrochemical Impedance Spectroscopy, Reflectance Absorption FT-IR, Attenuated Total Reflectance FT-IR, Ellipsometry, QCM Impedance Analysis, SPR and Atomic Force Microscopy (AFM)). The characterization applies equally to each of the carbohydrate on Table 1 to obtain structural, thickness, rigidity, orientation, stability, and surface coverage information of the immobilized carbohydrate films.

Carbohydrate-Lectin Array Fabrication (Two Dimension)

Using the optimal conditions obtained from above characterization, the carbohydrates are spotted to the gold sensor chips using an automatic arraying robot or manually. Shown in FIG. 21, for initial 5×5 carbohydrate lectin arrays, each horizontal row is spotted with identical sugar. The number of rows can be easily enlarged to include the replication experiments. The gold chips are incubated overnight to allow self-assemble process and coupling reaction to complete. After washing, the gold chips are ready for the profiling experiments.

Lectin Tagging of the Target Bacterial Cells for Binding

Figure 21A:
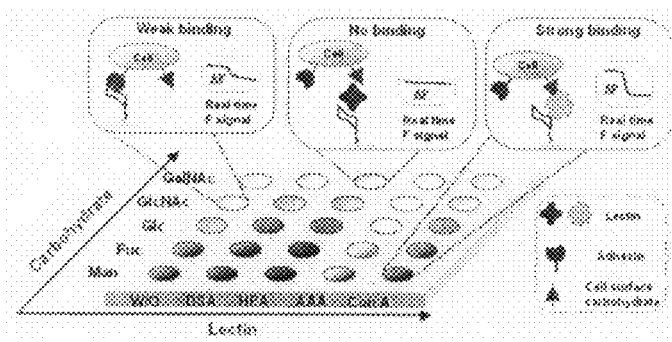
FIGS. 21A and 21B are carbohydrate-lectin 2D array for bacterial screening (21A); illustrative 2-D carbohydrate and lectin expression patterns (21B).

Bacteria in table 1 are purchased from ATCC and grown in culture. For example, the pure culture of *Escherichia coli* 157, (ATCC® 43895™) is grown in ATCC® medium at 37° C. for ~24 h in a shaking incubator. The viable cell number is determined by conventional agar plate counting. The fully characterized carbohydrate layers are first evaluated individually by EIS, QCM and SPR techniques for binding with their specific lectin to obtain the calibration curves to determine the optimal concentration needed to label the targeted bacteria with lectin. For our initial 5×5 carbohydrate lectin arrays, each of the bacteria grown in the culture are diluted and aliquot in identical five batch samples. As shown in FIG. 21, four of the five batch bacterial samples are tagged with a specific lectin (i.e. DSA, HPA, AAA and Con A) at the optimal lectin concentration for the binding experiments.

Binding and Detection

Figure 21B:
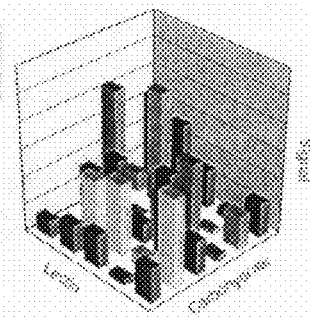

The carbohydrate microarray are incubated in the appropriate buffer (e.g. PBS). Then 20 µl or less of each of the five bacterial samples are added to each column of the array respectively (FIG. 21B). The real time frequency change vs. time is monitored for QCM measurement. The multi-channel QCM prototype and commercial QCM instruments (Preliminary study) are used. For impedance measurement, each bacterial sample is spiked with redox probe 1 mM $Fe(CN)_6^{3-/4}$ and the impedance is measured using PAR 2263 potentiostat.

Following the incubation for a desired period, a subsequent addition of the analyte (i.e. bacterial sample with or without lectin tags) is added. The real time, label free readout by QCM and EIS allows multiple additions of samples without washing steps. Therefore, using one chip, multiple quantitative analysis and monitoring bacterial surface carbohydrate and lectin expression are preferred in a dynamic real time manner.

Regeneration of the Chip

For pathogenic bacteria profiling and detection, once the gold sensor chip is exposed to the bacterial sample, it is considered to be contaminated and should be disposed or decontaminated. De-contamination can destroy the immobilized receptors and unsuitable for re-use. As carbohydrate modified piezoelectric crystals are inexpensive, i.e., it is affordable to use disposable transducers. The reversibility of the binding reaction is assessed to deliver the feasibility of continuous monitoring without calibration. The Au-array regeneration step is developed and optimized using a non-pathogenic *E Coli* Strain W 1485. After each round of experiment, the carbohydrate-bacteria and carbohydrate-lectin-bacteria complex is dissociated using standard methods such as a high salt solution or low pH. The condition will not harm the carbohydrate epitopes. This method is not expensive but it can cause significant degradation after several re-uses. Therefore it is safer practice to remove the whole carbohydrate-antigen complex or use freshly labeled crystals for each assay. Since the SAM template is used for immobilization of carbohydrate, the gold surface can be completely stripped through a reductive desorption process (i.e. carbohydrate complex-S-Au+e+$H^+$→carbohydrate complex-SH+Au) and characterized using electrochemical technique. The crystals can be cleaned with proper reagents and then relabeled with functionalized linkers for the new target application. This procedure can be repeated until the gold substrate is either too thin or becomes uneven, which will produce poor immobilization of the linkers.

Large Array Incorporating with Other Sugars and Antibodies

Four oligosaccharides (Sialyl $Le^x$, α-2,6 sialoside, GM3 and Gal-α,1,3-Gal trisaccharide) are included to observe the pattern (Table 3). Glycosyltransferase mediated glycosylation are employed starting from the monosaccharides or disaccharides.

TABLE 3

Lectin and carbohydrate specificity

| Lectin | Carbohydrate |
| --- | --- |
| *Maackia amurensis* (MAA) | GM3 |
| *Sambucus nigra* (SNA) | α-2,6 sialoside |
| *Lotus tetragonolobus* (Lotus A) | Sialyl $Le^x$ |
| *Griffonia simplicifolia* lectin-1-B4 (GSI-B4) | Galα-1,3-Gal trisaccharide |

Figure 22:
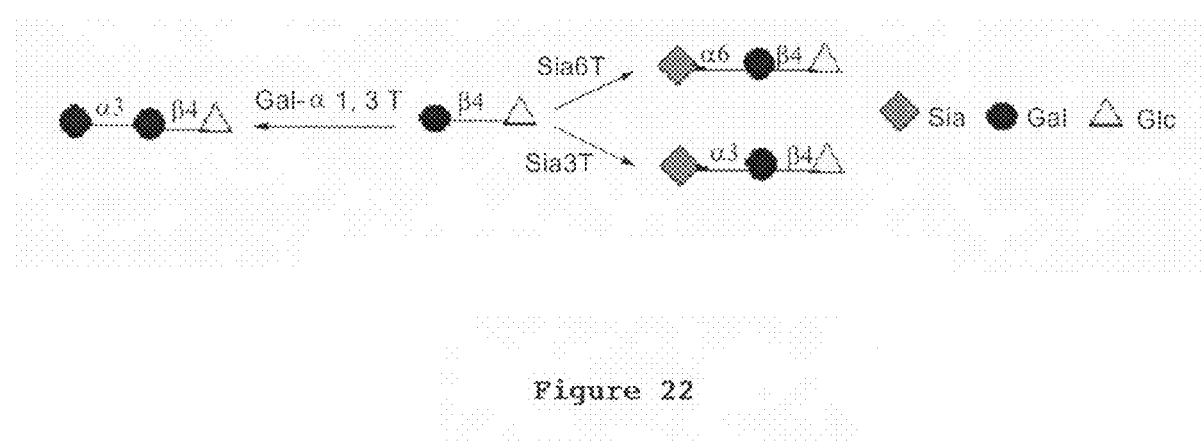
FIG. 22 is a synthetic scheme showing oligosaccharides are synthesized from azido lactose.

Specifically, using the corresponding glycotransferases and sugar donors, oligosaccharides are synthesized from azido lactose (FIG. 22). Several available anti-LPS carbohydrate antibodies can be added into the carbohydrate-lectin array.

The carbohydrate-lectin array offers wide flexibility in profiling cell surface carbohydrate and lectin expression. It overcomes the limitations of both carbohydrate array and lectin arrays and significantly expands research capacity in glycobiology. They can impact various fields including bacterial pathogenesis, tumor cell metastasis, and inflammation and provide a valuable tool for bacterial detection for bioterrorism defense, environmental pollutant monitoring, forensic analysis, biological research, and diagnosis for bacterial infection. The Anticipated Advantages of the 2D Lectin-Carbohydrate Microarray Are;

1. Selective. Carbohydrate-lectin array is highly selective due to the 2 dimensional fingerprints of cell surface carbohydrate and protein expression;
2. Sensitive. High density of expressed carbohydrates on bacterial cell surface and high density of carbohydrate recognition elements on sensor surface reduce the non-specific interaction and enhance the sensitivity;
3. Accurate. Orthogonal sensing by EIS and QCM reduce false positives. Pattern Recognition by sensor array further increases the accuracy;
4. Real time: QCM is real time and EIS is near real time measurement, allowing results to be obtained very quickly;
5. Non-destructive: The cells can be either harvested for test or monitored dynamically for other biological studies;
6. Long shelf-life: carbohydrates are more stable and smaller than antibody/nucleic acid, they rarely denature or lose activity;
7. Simple and low cost. It does not require process treatment to measure and does not require fluorescence labeling. EIS and QCM are low cost transduction mechanisms and ready for miniaturization using microsystem technologies permits batch fabrication and low cost manufacturing; and
8. Fast. One step detection and miniaturization helps to reduce the time to reach equilibrium.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A method of detecting a microorganism in a sample comprising:
   (a) providing (1) a biosensor device for detecting the microorganism in the sample comprising a solid substrate having a surface covalently bound to a capture agent having a saccharide moiety, (2) the sample, and (3) an unbound lectin capable of binding to the microorganism and to the saccharide moiety of the capture agent;
   (b) applying a polyethylene glycol thiol as a blocking agent to the solid substrate prior to applying the sample to the solid substrate to reduce nonspecific adsorption to the solid substrate;
   (c) applying the sample and the unbound lectin to the solid substrate with the capture agent having the saccharide moiety, for a time to bind the lectin to the saccharide moiety of the capture agent and the lectin to the microorganism to attach the microorganism to the solid substrate; and
   (d) detecting the microorganism attached to the solid substrate with the biosensor device.

2. The method of claim 1, wherein the substrate is provided as a component in a quartz crystal microbalance (QCM) device.

3. The method of claim 1, wherein the substrate is provided as a component in a surface plasmon resonance (SPR) device or an impedance device.

4. The method of claim 1, wherein:
   (i) the biosensor device comprises an array of solid substrates, each solid substrate having a surface covalently bound to a capture agent having a saccharide moiety, the saccharide moiety being different for at least some of the solid substrates such that the array of solid substrates has a plurality of different saccharide moiety types.

5. The method of claim 1, wherein:
   (i) the biosensor device comprises an array of solid substrates, each solid substrate having a surface covalently bound to a capture agent having a saccharide moiety.

6. The method of claim 1, wherein:
   (i) the biosensor device comprises an array of solid substrates, each solid substrate having a surface covalently bound to a capture agent having a saccharide moiety, the saccharide moiety being different for at least some of the solid substrates such that the array of solid substrates has a plurality of different saccharide moiety types;
(ii) the unbound lectin comprises a plurality of different unbound lectin types, each unbound lectin type being capable of binding to at least one of the saccharide moiety types of the array of solid substrates;
(iii) applying the sample and the unbound lectin in part (b) comprises applying a portion of the sample and an unbound lectin type to each of the solid substrates having a selected saccharide moiety type, the unbound lectin type being selected such that there is a plurality of combinations of the saccharide moiety type and the unbound lectin type in the array.

* * * * *

UNITED STATES PATENT AND TRADEMARK OFFICE
CERTIFICATE OF CORRECTION

PATENT NO.         : 8,088,596 B2
APPLICATION NO.    : 11/973772
DATED              : January 3, 2012
INVENTOR(S)        : Xiangqun Zeng and Zhihong Shen It is certified that error appears in the above-identified patent and that said Letters Patent is hereby corrected as shown below:

Column 28, line 59 (Claim 4) - should be added

--(ii) the unbound lectin comprises a plurality of different unbound lectin types, each unbound lectin type being capable of binding to at least one of the saccharide moiety types of the array of solid substrates;

(iii) applying the sample and the unbound lectin in part (b) comprises applying a portion of the sample and an unbound lectin type to each of the solid substrates having a selected saccharide moiety type, the unbound lectin type being selected such that there is a plurality of combinations of the saccharide moiety type and the unbound lectin type in the array.--

Column 28, line 62 (Claim 5) - "moiety." should be

--moiety, the saccharide moiety being different for at least some of the solid substrates such that the array of solid substrates has a plurality of different saccharide moiety types.--

Column 28, line 66 (Claim 6) - "having a saccharide moiety, . . ."
- should be --moiety.--
- should be deleted ", the saccharide moiety being different for at least some of the solid substrates such that the array of solid substrates has a plurality of different saccharide moiety types;"
- (ii) wording should be deleted
- (iii) wording should be deleted Signed and Sealed this
Seventh Day of August, 2012

David J. Kappos
*Director of the United States Patent and Trademark Office*